(12) United States Patent
Das et al.

(10) Patent No.: US 9,505,794 B2
(45) Date of Patent: Nov. 29, 2016

(54) RUTHENIUM (II) COMPLEXES, PREPARATION AND USES THEREOF

(71) Applicant: Council of Scientific and Industrial Research, New Delhi (IN)

(72) Inventors: Amitava Das, Pune (IN); Samit Chattopadhyay, Pune (IN); Vadde Ramu, Pune (IN); Nandaraj Taye, Pune (IN)

(73) Assignee: Council of Scientific and Industrial Research, New Delhi (IN)

( * ) Notice: Subject to any disclaimer, the term of this patent is extended or adjusted under 35 U.S.C. 154(b) by 0 days.

(21) Appl. No.: 14/878,568

(22) Filed: Oct. 8, 2015

(65) Prior Publication Data

US 2016/0102357 A1    Apr. 14, 2016

(30) Foreign Application Priority Data

Oct. 8, 2014  (IN) .......................... 2864/DEL/2014

(51) Int. Cl.
*C07F 15/00*    (2006.01)
(52) U.S. Cl.
CPC ................. *C07F 15/0053* (2013.01)

(58) Field of Classification Search
CPC .................... C07F 15/0053; C12Q 1/6886
USPC ...................................... 546/2, 10; 435/6.1
See application file for complete search history.

(56) References Cited

PUBLICATIONS

Ezadyar, S. Ali, et al., "Binuclear ruthenium(II) polypyridyl complexes: DNA cleavage and mitochondria mediated apoptosis induction", *Polyhedron*, 36(1), (2012), 45-55.
Gill, Martin R., et al., "A ruthenium(II) polypyridyl complex for direct imaging of DNA structure in living cells", *Nature Chemistry*, 1, (2009), 662-667.
Yu, Qianqian, et al., "Chiral Ruthenium(II) Polypyridyl Complexes: Stabilization of G-Quadruplex DNA, Inhibition of Telomerase Activity and Cellular Uptake", *PLOS One*, 7(12), e50902, (2012), 1-13.

*Primary Examiner* — Porfirio Nazario Gonzalez
(74) *Attorney, Agent, or Firm* — Schwegman Lundberg & Woessner, P.A.

(57) ABSTRACT

The present invention discloses novel Ruthenium (II) polypyridyl complexes, preparation and its application as DNA imaging agents.

11 Claims, 14 Drawing Sheets
(14 of 14 Drawing Sheet(s) Filed in Color)

RUTHENIUM (II) COMPLEXES, PREPARATION AND USES THEREOF

CLAIM OF PRIORITY

This application claims the benefit of priority of India Patent Application Serial No. 2864/DEL/2014, entitled "NOVEL RUTHENIUM (II) COMPLEXES, PREPARATION AND USES THEREOF," filed on 8 Oct. 2014, the benefit of priority of which is claimed hereby, and which is incorporated by reference herein in its entirety.

FIELD OF THE INVENTION

The present invention relates to novel Ruthenium (II) polypyridyl complexes, preparation and its application as DNA imaging agents in PFA fixed MCF-7 cells.

BACKGROUND AND PRIOR ART OF THE INVENTION

The development of molecular probes for selective DNA imaging is of great importance for studies in cell biology and clinical diagnosis. The commercially available DNA-specific dyes generally suffer from the poor water solubility and photo bleaching issues. In addition, dyes like DAPI (4',6-diamidino-2-phenylindole), and Hoechst have shorter life times, small stoke's shift value and require ultra-violet light illumination. Apart from these, auto fluorescence coming from the endogenous fluorophores (mitochondria, DNA and NADPH) also limit practical application of such dyes.

In this regard, Ru (II) polypyridyl complexes offer excellent luminescent properties and rich photochemistry. Their high photostablity, larger stoke's shift value (more than 150 nm) and solubility in aqueous environment makes such derivatives an ideal candidate for use as cellular imaging agent. Recently, Ru(II) complexes were used for imaging the structure of the DNA in live cells.

An article titled "A ruthenium(II) polypyridyl complex for direct imaging of DNA structure in living cells" published in NATURE CHEMISTRY, DOI: 10.1038/NCHEM.406, published in October 2009 discloses dinuclear Ru(II) complexes [(phen)$_2$Ru(tpphz)Ru(phen)$_2$]$^{4+}$ and [(bpy)$_2$Ru(tpphz)Ru(bpy)2]$^{4+}$ wherein, phen=1,10-phenanthroline, tpphz=tetrapyrido[3,2-a: 2',3'-c:3",2"-h:2'", 3'"-j]phenazine, as shown below, for use as DNA imaging agents with both luminescence and transition electron microscopy. However, these complexes are appear to be more of hydrophilic rather than lipophilic, limiting its cell diffusion across the membrane at low concentrations and therefore requires relatively in higher concentration for efficient uptake.

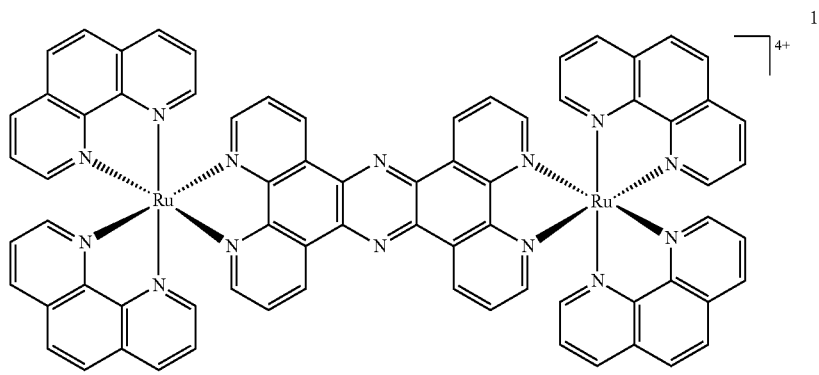

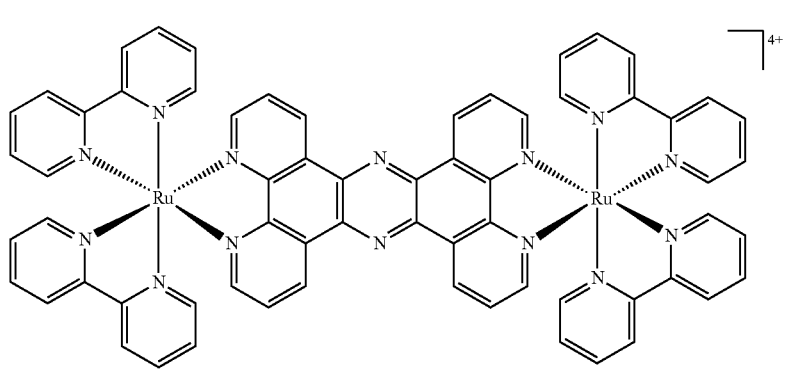

Another article titled "Binuclear ruthenium(II) polypyridyl complexes: DNA cleavage and mitochondria mediated apoptosis induction" published in Polyhedron, Volume 36, Issue 1, 4 Apr. 2012, Pages 45-55 discloses binuclear complexes of the type [Ru2(N—N)4(TBPhen2)]4+, where N—N=2,2'-bipyridine (bpy) (1), 1,10-phenanthroline (phen) (2), dipyrido[3,2-a:2',3'-c]phenazine (dppz) (3) and (TBPhen2)=bis-phenanthroline Troger's Base analogue. These complexes 1& 2 are found to induce apoptosis. Therefore, the complexes studied in this article are cytotoxic and hence are not useful for DNA imaging in cells.

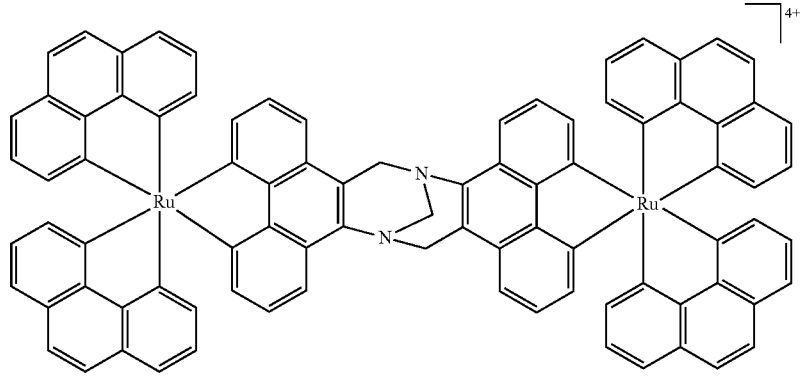

Another article entitled "Chiral Ruthenium (II) Polypyridyl Complexes: Stabilization of G-Quadruplex DNA, Inhibition of Telomerase Activity and Cellular Uptake" published in PLOS ONE, on December 2012, Volume 7, Issue 12, e50902, discloses Two ruthenium(II) complexes, L-[Ru(phen)2(p-HPIP)]2+ and D-[Ru(phen)2(p-HPIP)]2+ as telomerase inhibitors. These complexes are reported to have relatively higher selectivity to cancer cells than to normal cells.

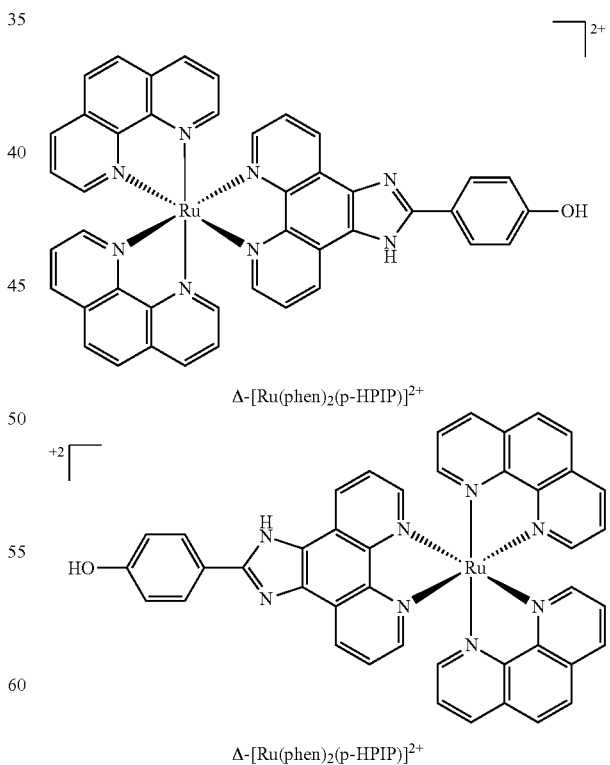

Further, most of the reported Ru(II) complexes are positively charged and possess limited cell membrane perme ability. This significantly restricts their potential application as cellular imaging agents. To overcome this issue of cell permeability, the common practice is of using serum free media, detergent (TritonX-100) or organic solvents such as DMSO, to make the cellular uptake more facile.

Recent reports demonstrated that polyarginine conjugated Ru(II) complexes can be targeted to the nucleus with the help of long chain polyarginine peptide. However, the preparation of polyarginine conjugated Ru(II) complexes not only involves much more synthetic effort, but also requires more incubation time. Also, the conjugation of polyarginine moiety may enhance the hydrophobicity of the Ru(II) complexes, thereby limiting their uptake to the lipid bilayer of the cell membrane. Some dinuclear Ru(II)polypyridyl complexes were also reported for cellular imaging but displays relatively poor solubility in pure water. Accordingly, DMSO has to be employed to prepare working stock solutions.

If the transition metal complexes need to be functioned as DNA imaging agents, it is required to possess low cytotoxicity and high membrane permeability in addition to high solubility and photo stability. From the above, it is evident that it is difficult to design such transition complexes that meet the requirement of the aforementioned properties.

Therefore there is a pronounced interest in the development of DNA specific probes which exhibits high water solubility, high photostablity, high membrane permeability, low toxicity and large stokes shifts to facilitate its application.

OBJECTIVE OF THE INVENTION

The main objective of the present invention is to provide novel Ruthenium(II) polypyridyl complexes that perform as efficient cellular DNA imaging probes in PFA fixed MCF-7 cells.

Another object of the invention is to provide a simple process for the preparation of Ru(II) polypryidyl complexes.

SUMMARY OF THE INVENTION

In accordance with the above objectives, the present invention provides novel Ruthenium (II) polypyridyl complexes of formula I as shown below.

Formula I

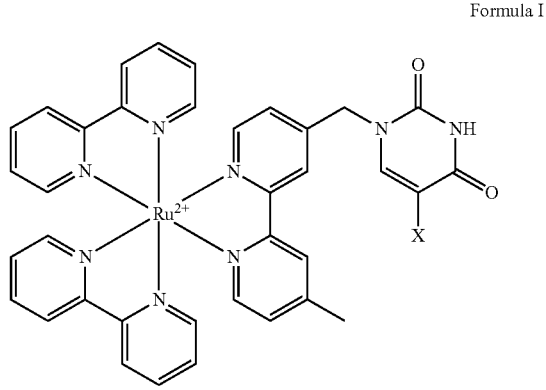

wherein, X is selected from hydrogen or fluorine.

Accordingly, in an aspect, the present invention encompasses novel Ruthenium (II) polypyridyl complexes of Formula 1 and 2.

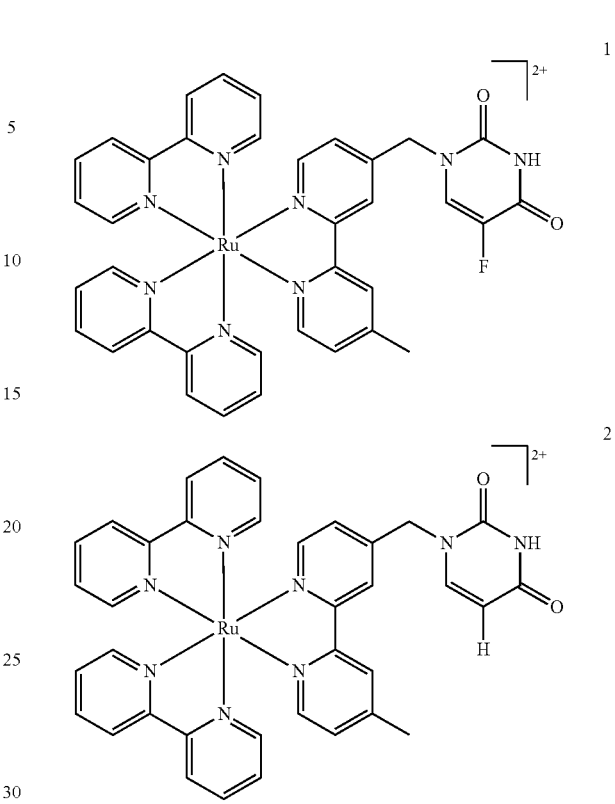

In another aspect, the invention provide a one step process for the synthesis of Ruthenium (II) polypyridyl complexes of Formula 1 and 2.

In another aspect, the properties of the Ruthenium (II) polypyridyl complexes of formula 1 & 2 are found to be highly water soluble, have large stokes shift (150-170 nm, relatively low-toxic (<350 µM), appreciably long lifetime (275-400 ns in aerated aqueous solution) and both excitation and fluorescence in visible region of the spectrum.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION OF THE INVENTION

Figure 1:
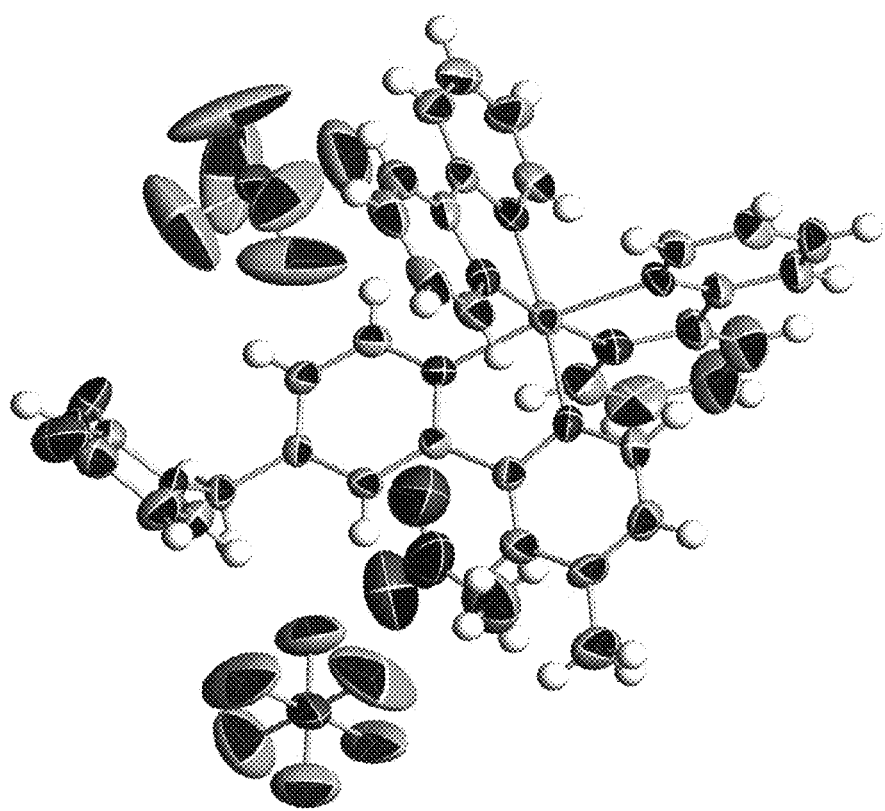
FIG. 1. ORTEP drawing of complex 2: Thermal ellipsoids set to 50% probability level.

The invention will now be described in detail in connection with certain preferred and optional embodiments, so that various aspects thereof may be more fully understood and appreciated.

Accordingly, the present invention provides novel Ruthenium (II) polypyridyl complexes, preparation and uses thereof.

In an embodiment the present invention provides novel Ruthenium (II) polypyridyl complexes of formula I as depicted below.

Formula I

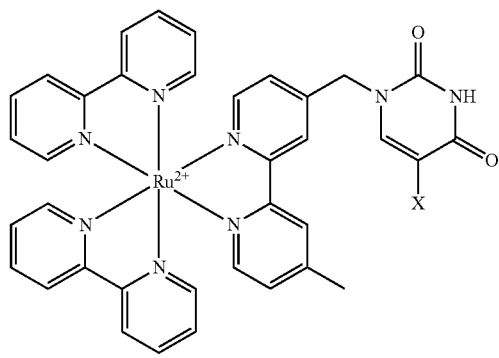

Wherein, X is selected from hydrogen and fluorine.

Accordingly, the present invention encompasses novel Ruthenium (II) polypyridyl complexes of formula 1 and formula 2.

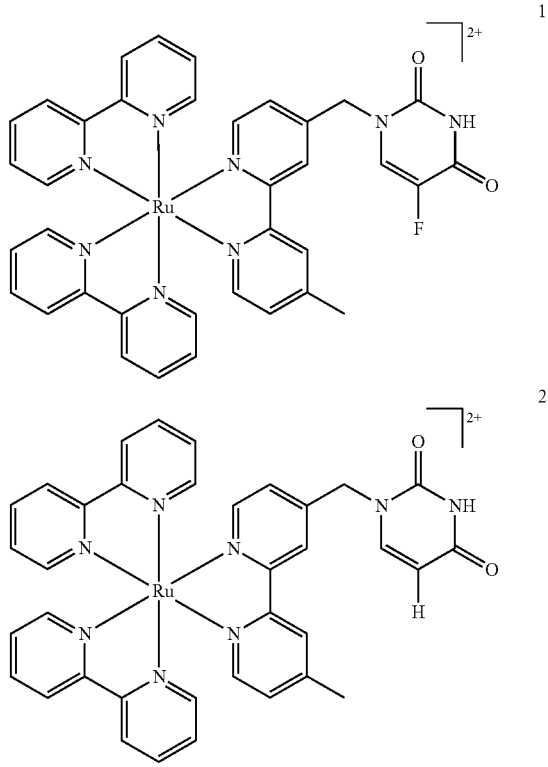

In another embodiment the present invention provides a single step process for the preparation of novel Ruthenium (II) polypyridyl complexes of formula I from novel ligand of formula 3,

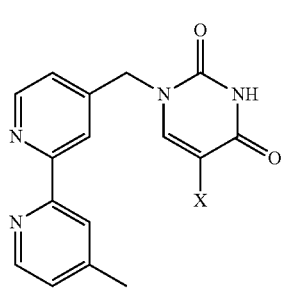

Wherein, X is selected from F or H,
Comprising:
a) Reacting [Ru(bpy)₂Cl₂]²⁺ compound of formula 4 with the ligand 3 in ethanol and
b) precipitating the desired Ruthenium(II) polypyridyl complexes of formula I by the addition of saturated aqueous potassium hexafluorophosphate (KPF₆) solution and
c) purifying the desired complexes of formula I.

The above synthetic route followed for the preparation of complexes of formula 1 and 2 is depicted below in Scheme 1.

Scheme: 1

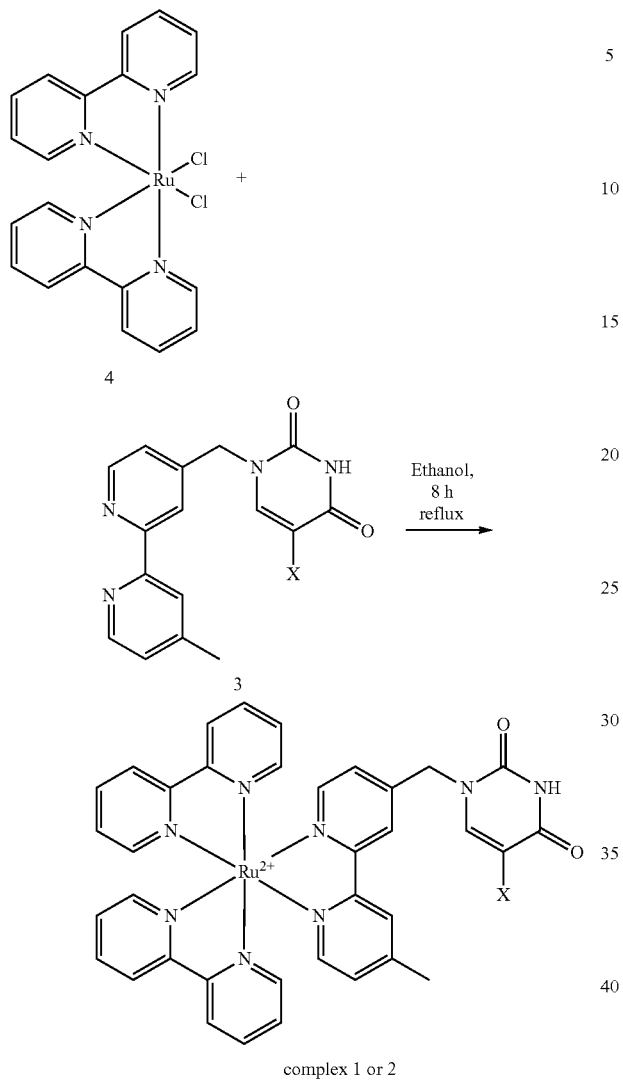

complex 1 or 2

Wherein, X is selected from F(complex 1) or H(complex 2).

In still yet another embodiment, the present invention provides novel Ruthenium (II) polypyridyl complexes of formula 1 (X=F) and formula 2 (X=H), wherein the said complexes are highly water soluble, relatively non-toxic, higher $^3$MLCT excited state lifetimes, exhibit absorbance (455 nm) and fluorescence (617 nm) maxima in visible region and possess large Stoke's shift (165 nm) compared to the traditional DNA staining agents. Therefore, the present invention provides novel Ruthenium (II) polypyridyl complexes of formula 1 and formula 2 wherein the said complexes are used for cellular DNA imaging.

For the purpose of the present invention, complex of formula 1 is chemically termed as {bis-(2,2'-bpy)-(5-fluoro-1-((4'-methyl-[2,2'-bipyridin]-4-yl)methyl)pyrimidine-2,4(1H,3H)-dione)}ruthenium(II) dichloride and complex of formula 2 is chemically termed as {bis-(2,2'-bpy)-(1-((4'-methyl-[2,2'-bipyridin]-4-yl)methyl)pyrimidine-2,4(1H,3H)-dione)}ruthenium(II) dichloride.

In another aspect the present invention provides a process for preparation of ligand 3, wherein compound of ligand 3 is selected from:

a. Ligand $L_1$: 5-fluoro-1-((4'-methyl-[2,2'-bipyridin]-4-yl)methyl)pyrimidine-2,4(1H,3H)-dione
b. Ligand $L_2$: 1-((4'-methyl-[2,2'-bipyridin]-4-yl)methyl)pyrimidine-2,4(1H,3H)-dione.
c. Ligand $L_3$: 4,4'-dimethyl-2,2'-bipyridine.

Accordingly, the invention provides a process for preparation of Ligand $L_1$ which comprises reacting 4-(bromomethyl)-4'-methyl-2,2'-bipyridine with 5-fluorouracil in presence of $K_2CO_3$ and KI in DMSO. Similarly, ligand $L_2$ is prepared by reacting 4-(bromomethyl)-4'-methyl-2,2'-bipyridine with Uracil in presence of $K_2CO_3$ and KI in DMSO. The ligands 1 & 2 are used for the preparation of complexes 1 & 2 of the invention.

In yet another aspect, a model complex 3 is prepared for comparing with the complexes 1 & 2. The model complex 3, ([Ru(bpy)2(L3)]2+; wherein, bpyis 2,2'-bipyridine & L3=4,4'-dimethyl-2,2'-bipyridine, as shown below.

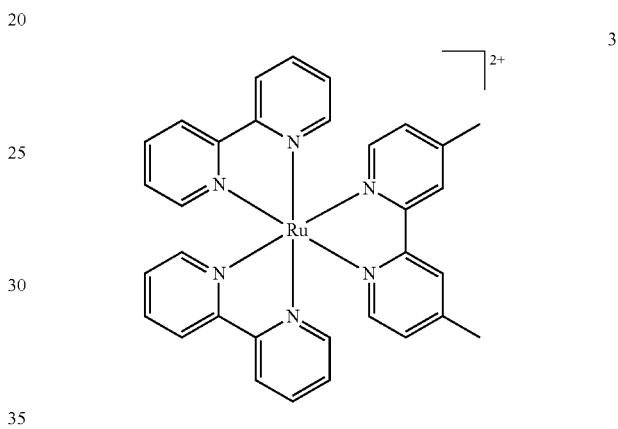

In yet another embodiment, Cl$^-$ ion is selected as counter anions for complexes 1, 2 & 3, to achieve the desired solubility in aq. buffer (Tris-HCl buffer, pH=7.4) media.

In another aspect, the structural elucidation of complexes 1, 2 & 3 are confirmed by single crystal X-ray structural analysis, $^1$H NMR, $^{19}$F NMR, EI mass spectrum etc.

Figure 20:
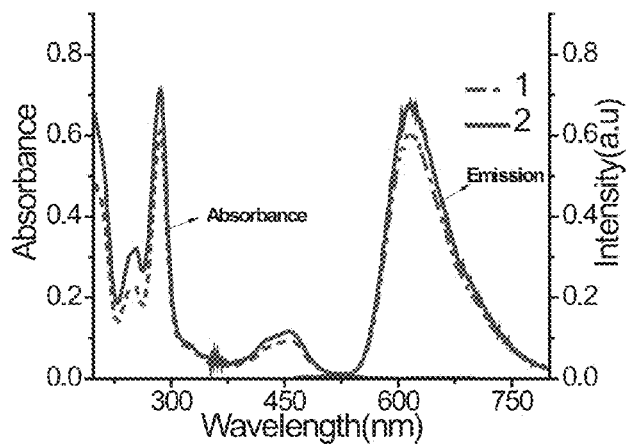
FIG. 20 Absorbance and emission spectra for 1 (blue line) and 2 (red dotted line).

Photophysical properties of the complexes 1, 2 recorded in pure aqueous medium are provided in table 3. Relative binding affinity of complexes 1, 2, and 3 towards calf-thymus DNA (CT-DNA) were evaluated using isothermal titration calorimetry (ITC) (FIG. 20). Association constants and thermodynamic parameters (Table 4) clearly reveal that the binding affinities for complexes 1 and 2 are much higher than that of model complex 3 towards CT-DNA. The binding affinity of all three complexes for the CT-DNA is 1>2>3.

In yet another embodiment, the invention provides evaluation of both the complexes 1 and 2 for their cytotoxicity, in order to extend its application as DNA imaging agents. The cytotoxicity studies confirm that both the complexes 1 & 2 showed insignificant cytotoxicity and a lipophilicity dependent cellular internalization process. Furthermore, when studied in MCF-7 cells, localization of complexes 1 and 2 were observed only in nucleus and such observation is hitherto unknown and unreported.

Figure 13:
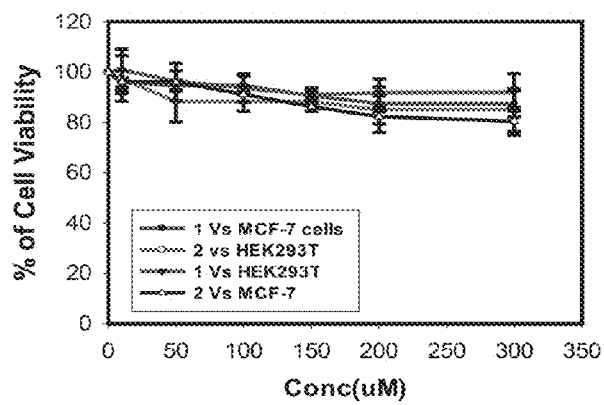
FIG. 13. Cell viability assay of 1 and 2 on MCF-7 and HEK293T cell line for 24 h incubation.

Cytotoxicity studies of complexes 1, 2, and 3 were investigated on MCF-7 cells using MTT (MTT=(3-(4,5-dimethylthiazol-2-yl)-2,5-diphenyltetrazolium bromide) assay methodology. The cell viability was found to be ≥85% after incubation with 300 μM of 1, 2, and 3 for 24 h. Thus, MTT assay confirmed that the insignificant toxicity of all three complexes towards MCF-7 cell lines (FIG. 13). Evaluated IC50 values were found to be ≥300 μM.

Figure 19:
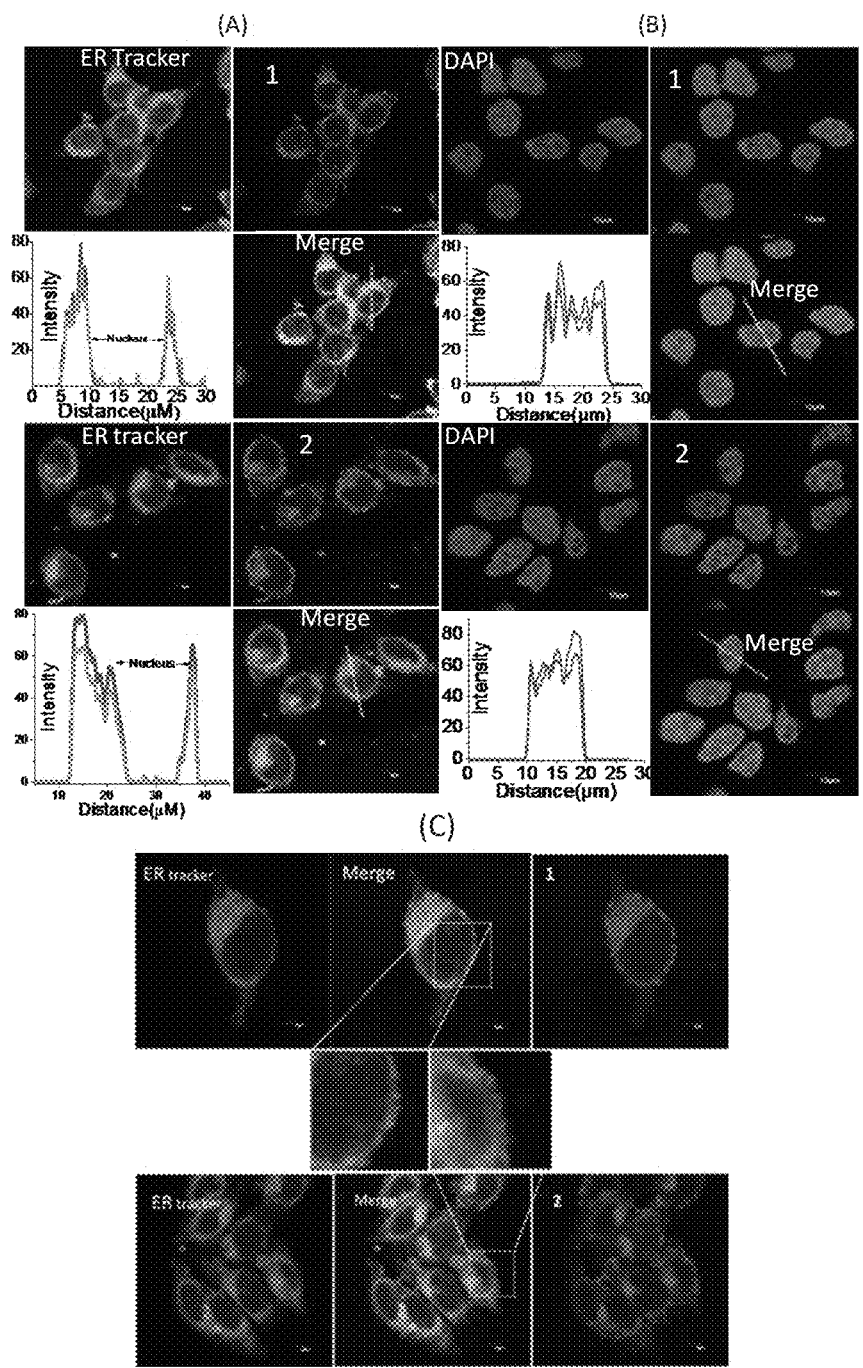
FIG. 19. CLSM images that shows the live cell uptake (A) and fixed cell staining (B) of 1 and 2. Enlarged view (C) of the live MCF-7 cells incubated with ER tracker green and complexes 1 and 2. Co-localization studies performed with ER-Tracker™ Green for live cells and with DAPI for fixed cells.

In the light of the negligible toxicity towards MCF-7 cells, the application of the above complexes as potential as imaging agents was explored in live MCF-7 cells by incubating the cells separately with 50 μM of 1, 2, and 3 at 37° C. A close comparison of the confocal laser scanning microscopic (CLSM) images as well as the images of the co-staining experiments with well-known ER staining agent clearly concludes that intracellular emission for 1 and 2 were found to be exactly superimposed with those for ER-Tracker™ Green (FIG. 19A) Also, distinct emission of 1 and 2 was also observed from the cell membrane, indicating that the cell membrane was also a target for the complexes 1 and 2. Identical studies with complex 3 did not show any such specificity towards lipid dense regions like endoplasmic reticulum (ER) or cell membrane. Also, the extent of cellular uptake for complex 3 was found to be less as compared to the complexes 1 and 2. The enlarged confocal images for complexes 1 and 2 (FIG. 19C) reveals dot-like structures with red fluorescence in bright-field microscopy, a pattern that is observed earlier for localization of lipophilic reagents at the cell membrane, which are also observed to be scattered in the cytoplasm suggests that the complexes were also sequestered in cytoplasmic vacuoles.

Partition coefficients (log P) for these three complexes were evaluated by shake-flask method and these were correlated to the lipophilicity of respective complexes. Lipophilicity of the complexes 1 (log P=−0.85), 2 (log P=−0.50), and 3 (log P=−1.1) were evaluated. These data clearly reveal that log P is the highest for complex 2 followed by 1 and 3 as shown in (table 2).

In another embodiment, co-staining experiments were performed with DAPI, a commonly used commercial nuclear staining agent. For cells treated with complexes 1 and 2, CLSM images were recorded following excitation with 442 nm laser and intra cellular emission of respective complexes were observed at 620 nm. Superimposed fluorescence intensity profile plots (FIG. 19B) of the intracellular emission signals of DAPI with those of complexes 1 or 2, confirmed that both complexes were as efficient as DAPI in staining the nucleus of the MCF-7 cells.

Figure 22:
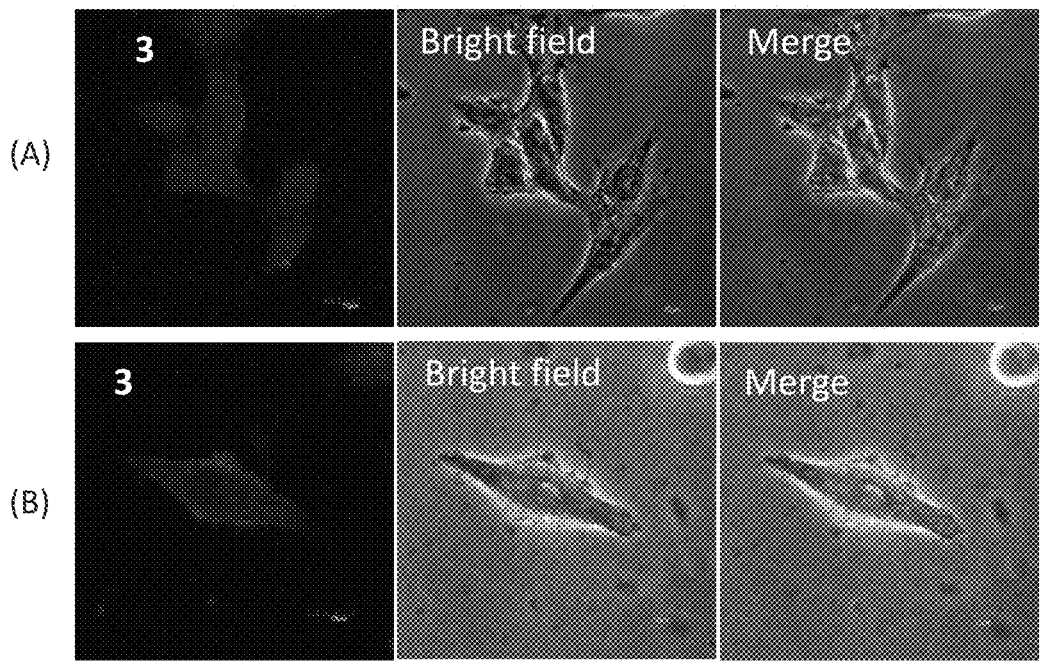
FIG. 22. a) CLSM images of fixed MCF-7 cells stained with 3 for 4 h b) Live MCF-7 cells stained with 3
FIG. 23. Live MCF-7 cells incubated with complexes 1 and 2 at 4° C.
Figure 23:
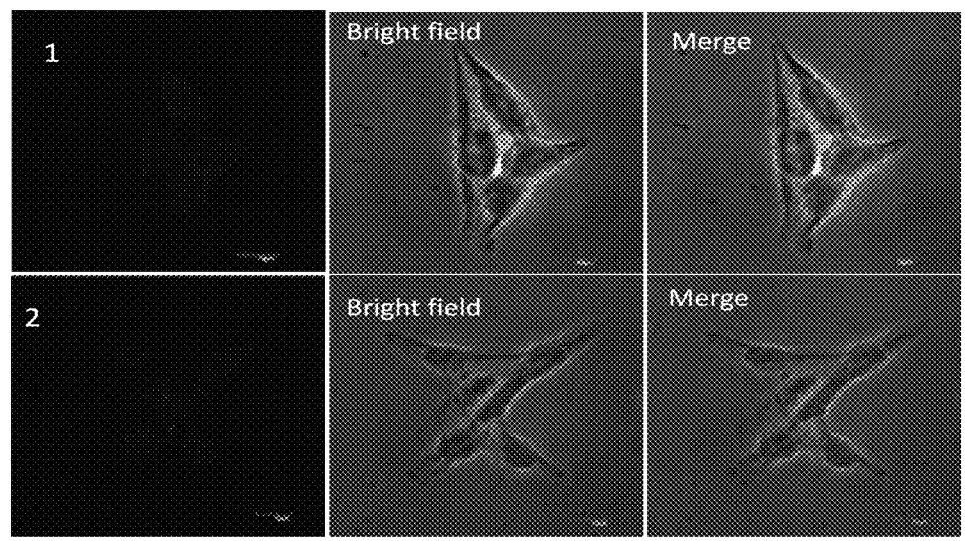
Figure 24:
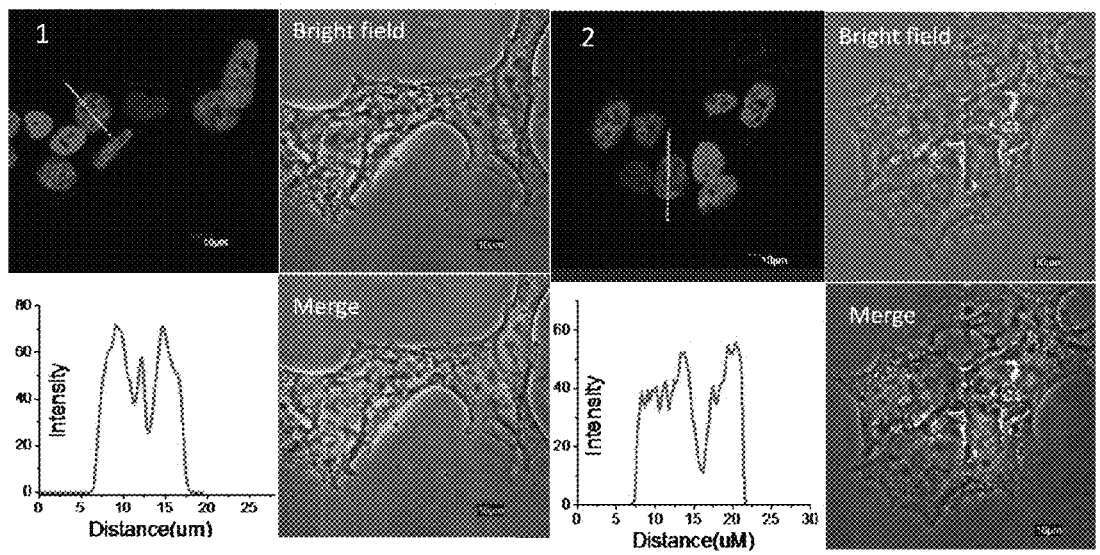
FIG. 24. PFA fixed MCF-7 cells incubated with 1 and 2 without DAPI.

However, complex 3 resulted in non-specific staining of cellular compartments in fixed cells and CLSM images revealed a non-specific internalization of complex 3 in cytoplasm and nucleus of fixed and live MCF-7 cells (FIG. 22 a & b). To ensure that DAPI had no influence in internalization of the complexes 1 and 2, identical experiments with fixed MCF-7 cells in absence of DAPI were performed (FIG. 22 c) and a distinct red emission were observed from the nucleus. Luminescence intensity profile plots confirmed that the emission was actually from the nucleus.

Figure 17:
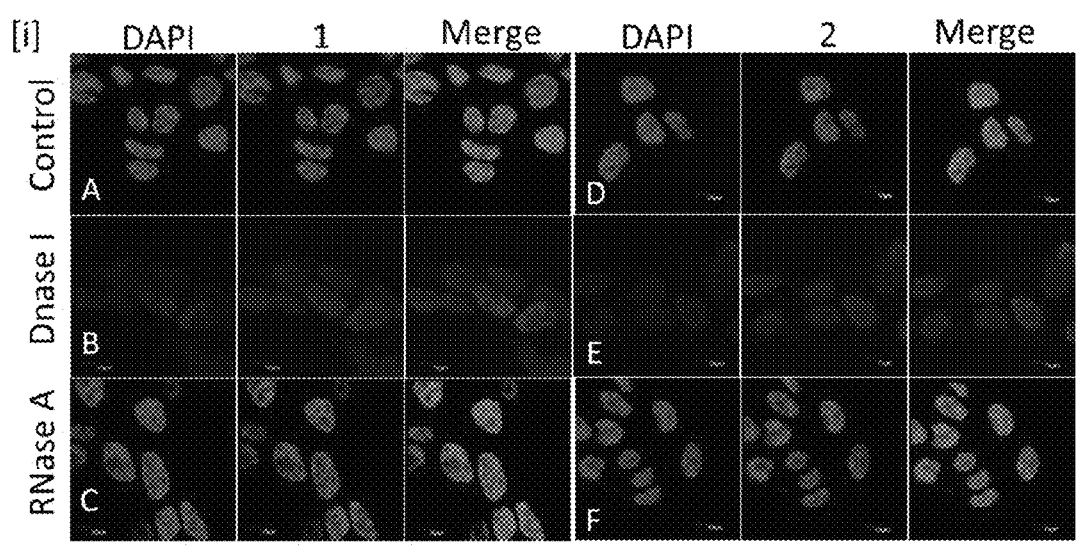
FIG. 17. CLSM images of MCF-7 cells incubated with complexes 1(A and B), 2(C and D) after treatment with RNase (A, C) and DNase (B, D).
Figure 18:
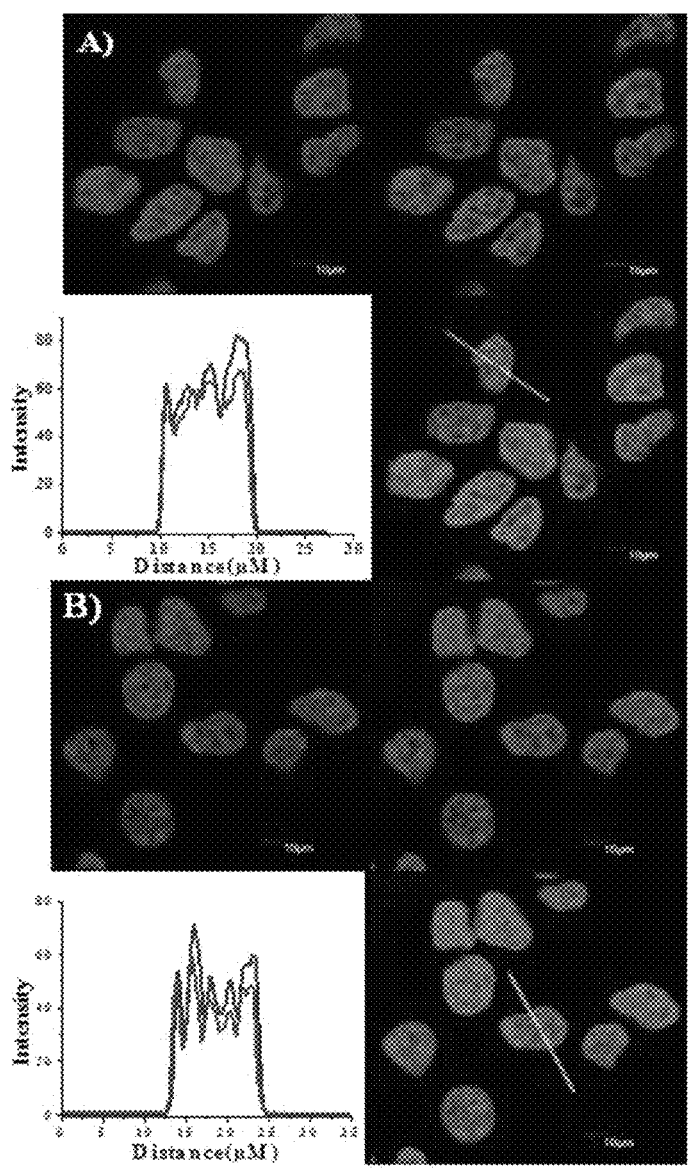
FIG. 18. CLSM image that shows cellular uptake and nuclear staining of MCF-7 cell s incubated for 2 h with 1 (20 µM) (Fig. A) and 2 (20 µM) (Fig. B) in serum containing media. The exact overlap of the two fluorescence profile represents that 1, 2 and DAPI are present at the cell nucleus. Intensity profiles plotted using ImageJ software.

Further, in order to check the preferential binding of these two reagents to nuclear DNA, deoxyribonuclease (DNase I) and ribonuclease (RNase A) digest experiments were carried out. DNase I is an enzyme that catalyzes the hydrolytic cleavage of phosphodiester linkages in the DNA and RNase A is a type of nuclease that catalyzes the degradation of RNA into smaller components. DAPI was used for control experiments. Comparison of the CLSM images of the cells pretreated with DNase I (FIG. 17) clearly revealed that the intracellular fluorescence intensities of complex 1 and 2 from the nucleus of MCF-7 cells were significantly reduced for cells that were pre-treated with DNase I and not for those pre-treated with RNase A. This further confirms that complexes 1 and 2 are mainly targeting nuclear DNA in the fixed cell nucleus.

In yet another embodiment, photostability of these two complexes 1 & 2 compared with that for DAPI dye by using confocal microscopy. The fluorescence intensity of DAPI upon continuous irradiation in fixed MCF-7 cells (at 359 nm for 300 sec) was drastically reduced, whereas, fluorescence intensity of complexes 1 and 2 were only reduced by ~20% upon exposure at 442 nm for 300 sec, reflecting the photostability of these two fluorescent complexes 1 & 2 as staining reagents.

Thus, the present invention provides the Ruthenium (II) polypyridyl complexes of formula I, for use as DNA imaging agents.

In a further embodiment, the invention provides method of imaging DNA in a tumor cell, which method comprises contacting the Ruthenium (II) polypyridyl complexes of formula I with cell nucleus to obtain the images of DNA.

The method according to the invention, the tumor/cancer cell may be selected from breast cancer; epithelial cancer, lung cancer, ovarian carcinoma, pancreatic carcinoma, prostate cancer or colorectal carcinoma.

In yet another embodiment, the invention provides a composition comprising Ruthenium (II) polypyridyl complexes of formula I along with one or more pharmaceutical carriers for use as DNA imaging agent.

The following examples, which include preferred embodiments, will serve to illustrate the practice of this invention, it being understood that the particulars shown are by way of example and for purpose of illustrative discussion of preferred embodiments of the invention.

EXAMPLES

Example 1

Experimental Details

Materials and Methods:

All chemicals were purchased from Sigma Aldrich unless otherwise indicated. All solvents were dried and distilled prior to use following standard procedures. $^1$H NMR spectra were recorded on a Bruker 500 MHz FT NMR (model: Advance-DPX 500) spectrometer at room temperature. ESIMS measurements were carried out on a Waters QTof-Micro instrument. UV-Vis spectra were obtained by using a Cary 500 scan UV-Vis spectrometer. The CT-DNA concentration per nucleotide was determined by absorption spectroscopy by using the molar absorption coefficient (6600 $mol^{-1}dm^3cm^{-1}$) at 260 nm. The emission spectra were obtained using Edinburgh instrument Xe-900 spectro fluorometer.

Synthesis

The ligands $L_1$ and $L_2$ were prepared by alkylation of 4-(bromomethyl)-4'-methyl-2,2'-bipyridine in DMSO directly with 5-fluorouracil at $N^1$ position to give 5-fluoro-1-((4'-methyl-[2,2'-bipyridin]-4-yl)methyl)pyrimidine-2,4 (1H,3H)-dione ($L_1$), and with uracil to give 1-((4'-methyl-[2,2'-bipyridin]-4-yl)methyl)pyrimidine-2,4(1H,3H)-dione ($L_2$). Reaction of these two ligands with [Ru(bpy)$_2$Cl$_2$] .2H$_2$O in ethanol for 8 h under reflux conditions afford a deep orange colored complexes 1 and 2 purified by column chromatography (silica 100-200 mesh and acetonitrile as eluent) and characterized using standard analytical techniques. Ligand L3 (4,4'-dimethyl-2,2'-bipyridine) was obtained from Sigma-Aldrich and used without further purification for the synthesis of complex 3.

Example 2

Synthesis of $L_1$

Figure 3:
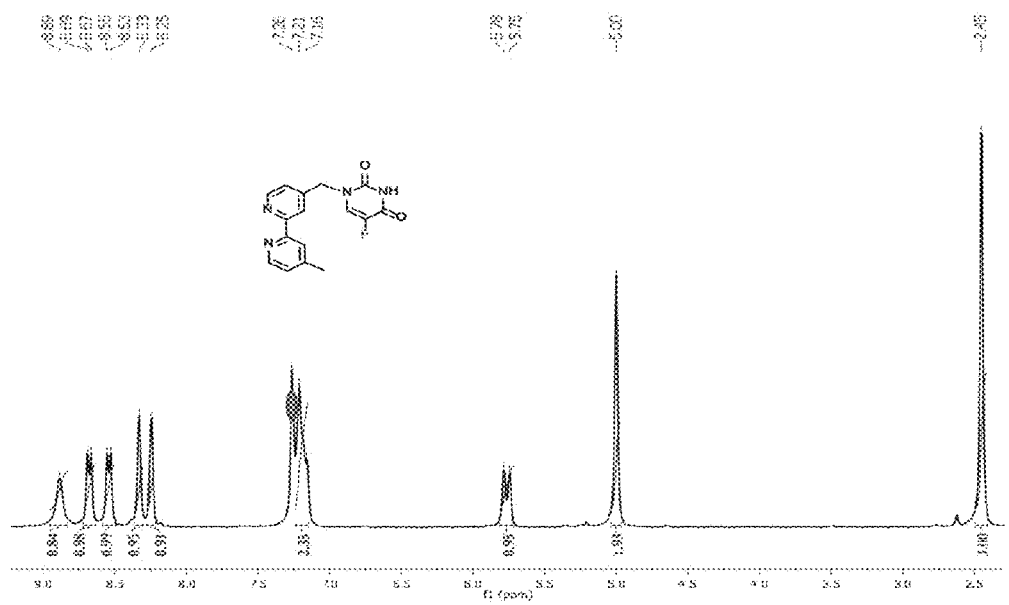
FIG. 3. $^1$H NMR for the ligand $L_1$ recorded in chloroform-$d_3$, the solvent peak was highlighted in blue circle.
Figure 4:
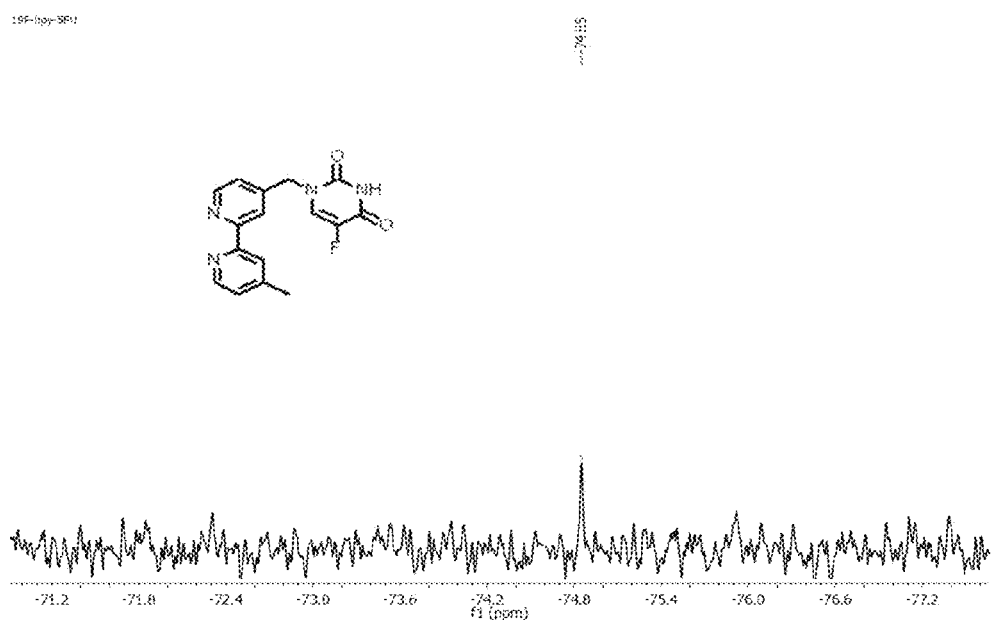
FIG. 4. $^{19}$F NMR for the ligand $L_1$ recorded in acetonitrile-$d_3$.
Figure 5:
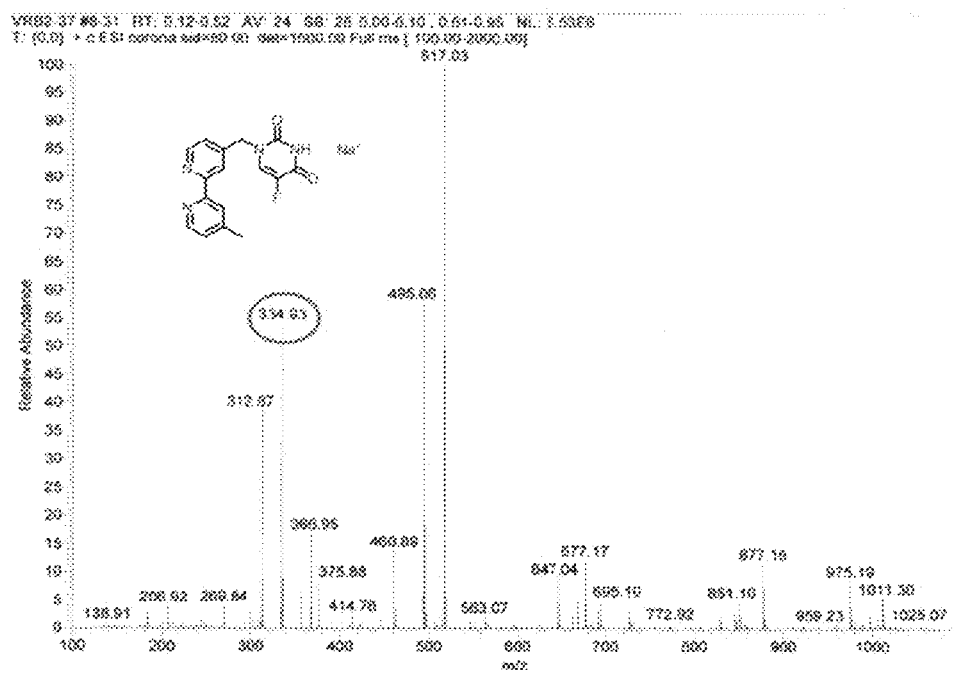
FIG. 5. ESI mass spectrum for the ligand $L_1$.
Figure 6:
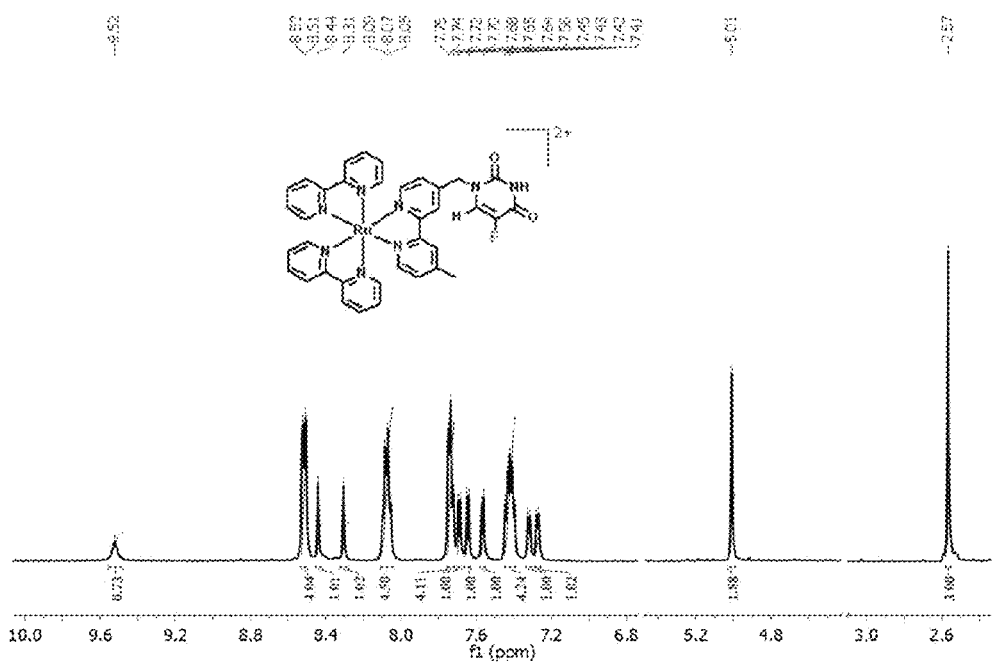
FIG. 6. $^1$H NMR for the complex 1 recorded in acetonitrile-$d_3$
Figure 7:
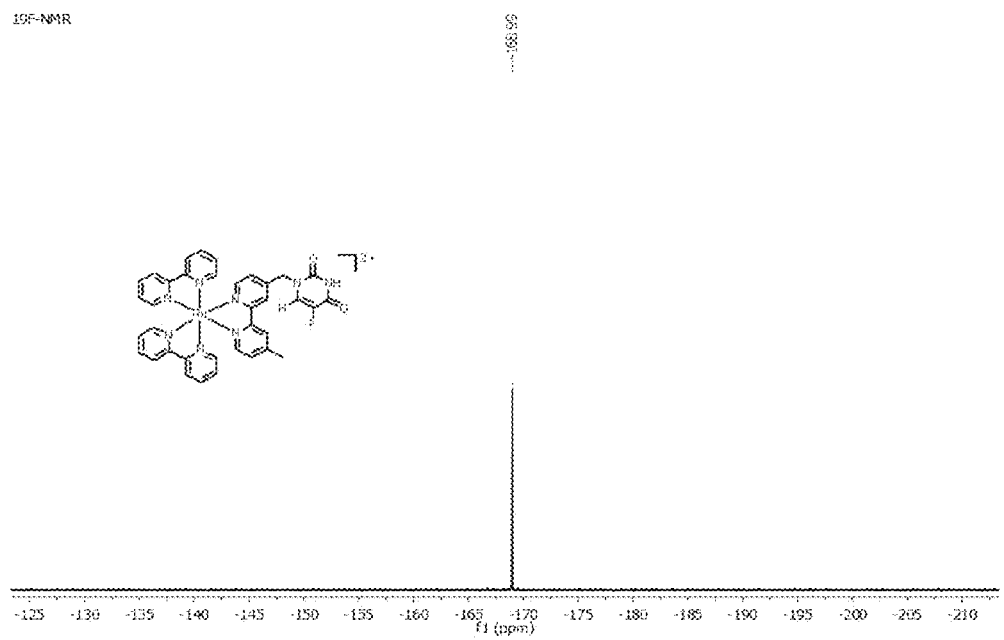
FIG. 7. $^{19}$F NMR for the complex 1 recorded in acetonitrile-$d_3$
Figure 8:
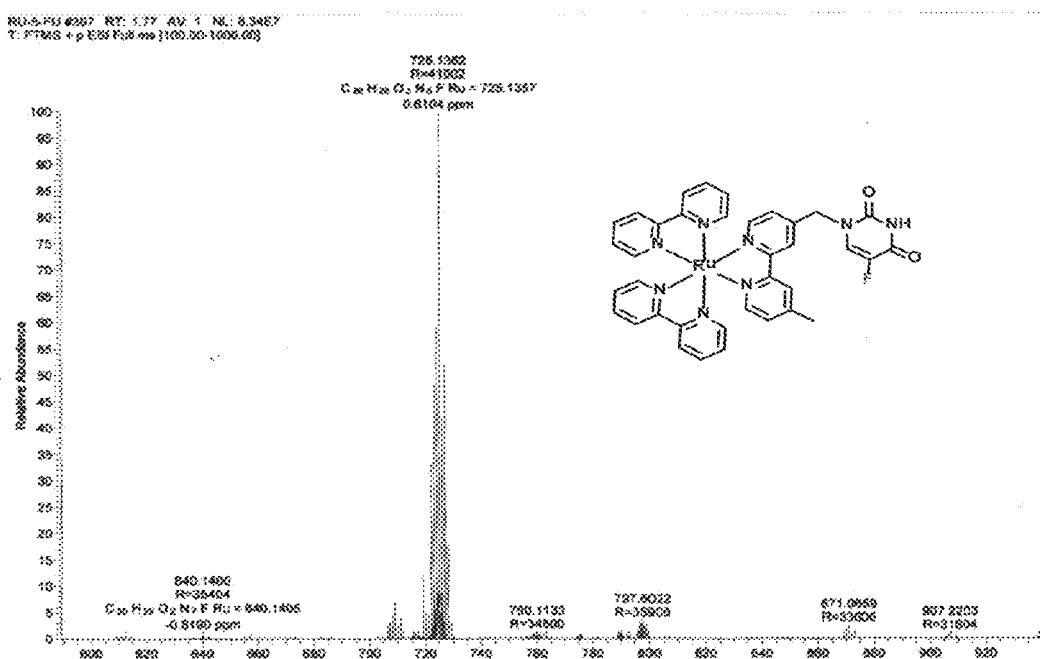
FIG. 8. ESI-HRMS for the complex 1.

A mixture of 5-fluorouracil (0.130 g, 1 mmol), $K_2CO_3$ (0.276 g, 2.0 mmol) and KI (ca. 25 mg) in 10 mL of DMSO was stirred under $N_2$ for 10 min. 4-(bromomethyl)-4'-methyl-2,2'-bipyridine (0.644 g, 2.45 mmol) predissolved in DMSO (5 mL) was then slowly added via a syringe and the resultant chocolate brown mixture was stirred under $N_2$ at room temperature for 3 h. Water (100 mL) was then added and the suspension was extracted with dichloromethane. The collected organic layers were dried over anhydrous sodium sulphate and the solvent removed in vacuum to give a half-white solid. The crude was subjected to the silica column chromatography using dichloromethane and acetone as solvent mixture 99:1% (v/v). The second spot from the bottom on the TLC plate was collected as $L_1$ (0.150 g, 48%). Electron impact (EI) mass spectrum: m/z=334.93[$L_1$+Na$^+$]. $^1$H NMR (200 MHz, methanol-d$_4$) $\delta_H$ 8.89 (1H, s), 8.68 (d, 1H, J=4.8 Hz), 8.54 (d, 1H, J=4.8 Hz), 8.33 (1H, s), 8.25 (1H, s), 7.19 (d, 2H, J=10.3 Hz), 5.77 (d, 1H, J=7.7 Hz), 5.00 (2H, s), 2.45 (1H, s). $^{19}$F NMR (400 MHz, MeOD-d$_4$) $\delta$ −74.85 ppm. (Refer FIG. 3, 4, 5)

Synthesis of $L_2$

Figure 9:
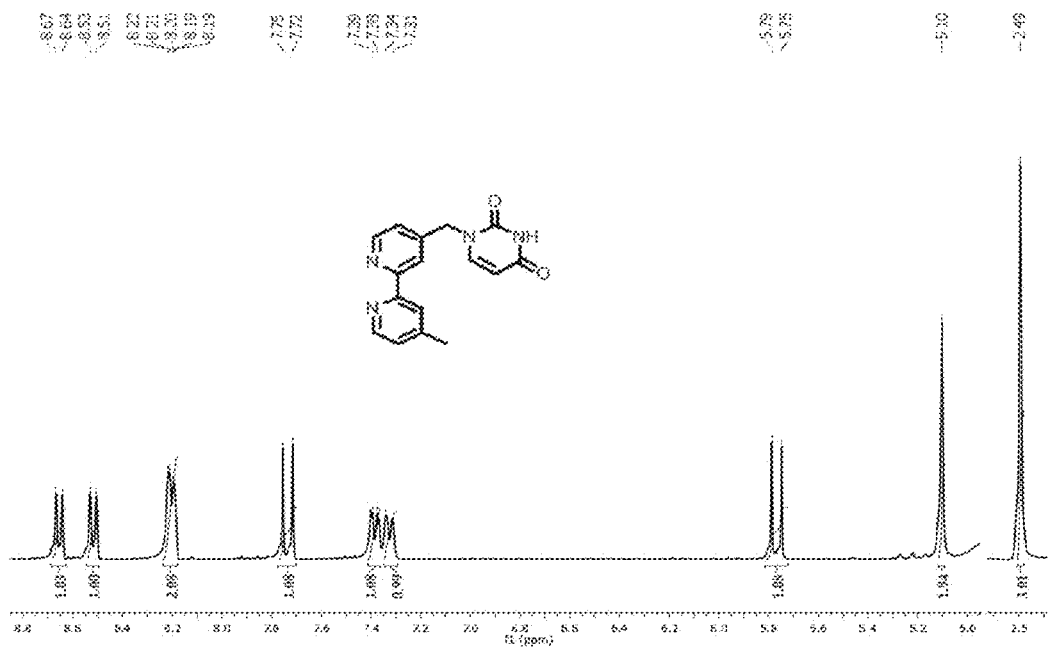
FIG. 9. $^1$H NMR spectrum of the ligand $L_2$.
Figure 10:
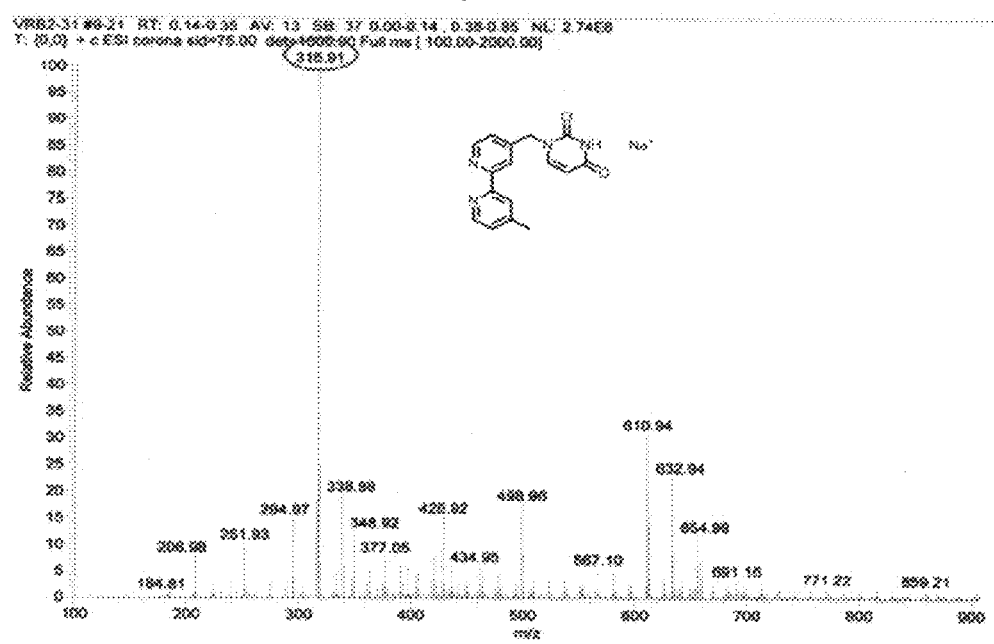
FIG. 10. ESI mass spectrum for the ligand $L_2$.
Figure 11:
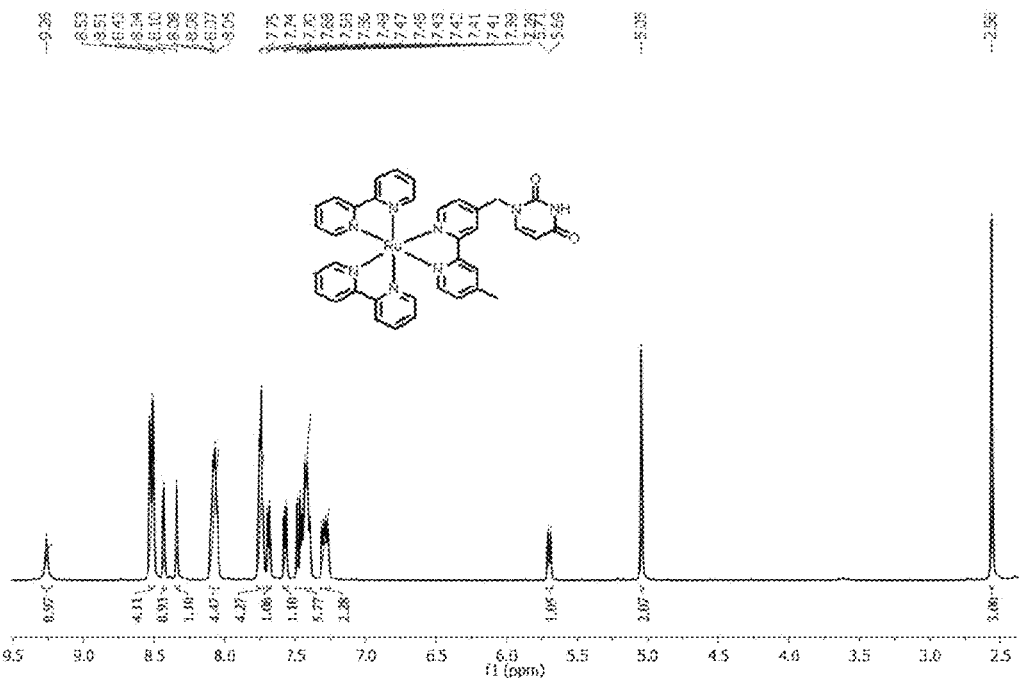
FIG. 11. ¹H NMR spectrum for complex 2 recorded in acetonitrile-d₃.
Figure 12:
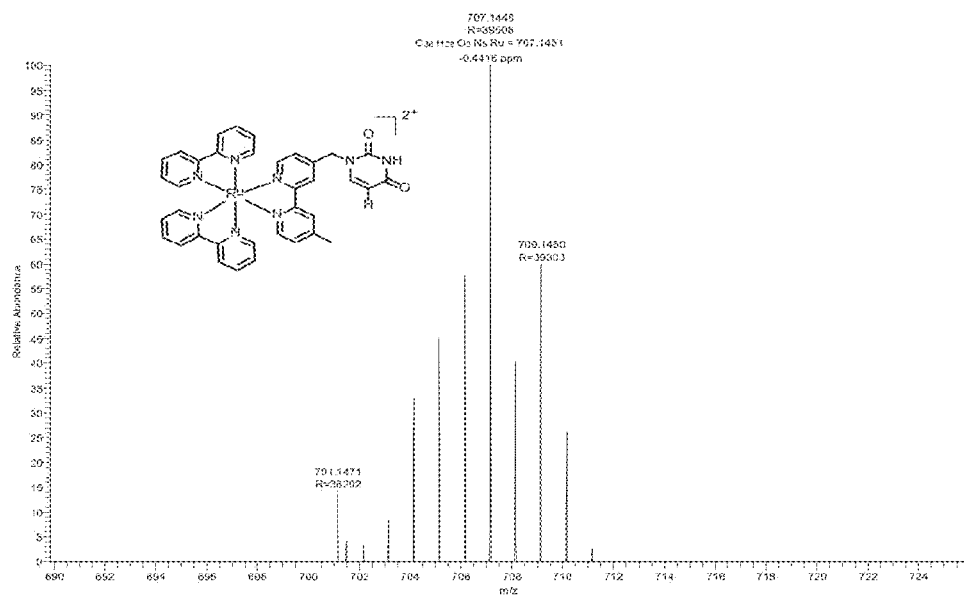
FIG. 12. ESI-HRMS for complex 2.

A mixture of uracil (0.112 g, 1 mmol), $K_2CO_3$ (0.276 g, 2 mmol) and KI (ca. 25 mg, a catalytic amount) in 10 mL of DMSO was stirred under $N_2$ for 10 min. 4-(bromomethyl)-4'-methyl-2,2'-bipyridine (0.644 g, 2.45 mmol) predissolved in DMSO (5 mL) was then slowly added via a syringe and the resultant chocolate brown mixture was stirred under $N_2$ at room temperature for 3 h. Water (100 mL) was then added and the suspension was extracted with dichloromethane. The collected organic layers were dried over anhydrous sodium sulphate and solvent was removed in vacuum to give a half-white solid. The crude was subjected to the silica column chromatography using dichloromethane and acetone as eluent 99:1% (v/v). The second spot on the TLC plate was collected as $L_2$ (0.145 g, 49.26%). Electron impact (EI) mass spectrum: m/z=316.91[$L_2$+Na$^+$]; $^1$H NMR (200 MHz, MeOD) $\delta_H$ 8.65 (d, 1H, J=5.7 Hz), 8.52 (d, 1H, J=4.8 Hz), 8.24-8.18 (2H, m), 7.73 (d, 1H, J=7.9 Hz), 7.38 (d, 1H, J=3.4 Hz), 7.32 (d, 1H, J=6.6 Hz), 5.77 (d, 1H, J=7.9 Hz), 5.10 (2H, s), 2.49 (3H, s). (Refer FIG. 9, 10)

Example 3

Synthesis of [Ru(bpy)$_2$(L$_1$)](PF$_6$)$_2$ (1); [Ru(bpy)$_2$(L$_2$)](PF$_6$)$_2$ (2) And [Ru(bpy)$_2$(L$_3$)](PF$_6$)$_2$ (3)

Complexes 1 2 and 3 were prepared using the reaction of [Ru(bpy)$_2$Cl$_2$]$^{2+}$ (0.145 g, 0.3 mmol) with the appropriate ligand L$_1$ (0.112 g, 0.3 mmol) or L$_2$ (0.105 g, 0.36 mmol) or L$_3$ (0.05 g, 0.3 mmol) in ethanol under reflux condition for 8 h. After cooling, addition of saturated aqueous potassium hexafluorophosphate (KPF$_6$) solution precipitated out the complexes as orange red solids. Which were filtered off using G4 glass cantered crucible. The precipitate washed with Millipore water (3 mL×5) followed by diethyl ether and dried over $P_2O_5$ in desiccator. The both compounds were purified by silica gel (100-200 mesh) column chromatography using acetonitrile and saturated KPF$_6$ solution 98:2% (v/v) as eluent.

Characterization of Complex 1

Figure 2:
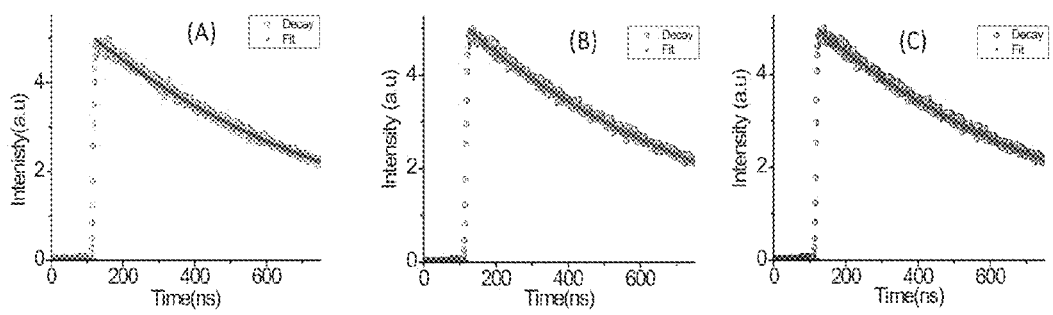
FIG. 2. Fluorescence life time decay for the complex 1(A) 2(B) and 3(C) fitted with single exponential. Time correlated single photon counting studies (TCSPC) were performed in aqueous medium. Excitation source: 443 nm laser.

Yield: (0.165 g, 0.16 mmol) Electron impact (EI) mass spectrum: m/z for 1$^{2+}$=725.1362 found; 725.1357 calculated [M-2PF$_6$]$^+$; $\delta_H$ (500 MHz, CD$_3$CN) 9.52 (1H, s), 8.51 (5H, d, J=7.4), 8.44 (1H, s), 8.31 (1H, s), 8.07 (5H, t, J=7.8), 7.73 (5H, t, J=6.6), 7.69 (1H, d, J=5.8), 7.64 (1H, d, J=6.2), 7.57 (1H, d, J=5.8), 7.46-7.38 (5H, m), 7.32 (1H, d, J=5.4), 7.27 (1H, d, J=5.6), 5.01 (2H, s), 2.57 (3H, s); $^{19}$F NMR (400 MHz, CD$_3$CN) $\delta$ −168.99 ppm. (FIG. 2,6,7,8);

Characterization of Complex 2

Yield: (0.159 g, 0.16 mmol) Electron impact (EI) mass spectrum: m/z for 2$^{2+}$=707.1448 found, 707.1451 calculated, [M-2PF$_6$]$^+$; $\delta_H$ (400 MHz, CDCl$_3$) 9.26 (1H, s), 8.52 (4H, d, J=8.0), 8.43 (1H, s), 8.34 (1H, s), 8.10-8.04 (4H, m), 7.75 (4H, d, J=4.5), 7.69 (1H, d, J=5.8), 7.57 (1H, d, J=5.7), 7.49-7.39 (5H, m), 7.31-7.25 (2H, m), 5.70 (1H, d, J=7.8), 5.05 (2H, s), 2.56 (3H, s). (FIG. 1,2,11,12)

Crystal structure and refinement details of complex 2 are provided in table 1.

Characterization of Complex 3

Yield: (0.151 g, 57%) ESI-MS: m/z for M$^{2+}$=299.07. $^1$HNMR (200 MHz, CD3CN) 8.58 (2H, s), 8.54 (2H, s), 8.43 (2H, s), 8.14-8.04 (4H, m), 7.80 (4H, d, J=5.6), 7.60 (2H, d, J=5.8), 7.50-7.40 (4H, m), 7.31-7.26 (2H, m), 2.57 (6H, s). Elemental analysis (as chloride salt). Calcd: C, 57.49; H, 4.22; N, 12.57. Found: C, 57.4; H, 4.2; N, 12.48.

Example 4

Single Crystal X-Ray Diffraction Studies and Crystal Structures of Complex 2

As-synthesized crystal of complex 2 was coated with paratone-N and placed on top of a nylon cryoloop (Hampton research) and then mounted in the diffractometer. The data collection was done at 298 K. The crystal was mounted on a Super Nova Dual source X-ray diffractometer system (Agilent Technologies) equipped with a CCD area detector and operated at 250 W power (50 kV, 0.8 mA) to generate Mo K$\alpha$ radiation ($\lambda$=0.71073 Å) and Cu K$\alpha$ radiation ($\lambda$=1.54178 Å) at 298 K. Initial scans of each specimen were performed to obtain preliminary unit cell parameters and to assess the mosaicity (breadth of spots between frames) of the crystal to select the required frame width for data collection. CrysAlis$^{Pro}$ program software was used suite to carry out overlapping $\phi$ and $\omega$ scans at detector (2$\theta$) settings (2$\theta$=28). Following data collection, reflections were sampled from all regions of the Ewald sphere to redetermine unit cell parameters for data integration. In no data collection was evidence for crystal decay encountered. Following exhaustive review of collected frames the resolution of the dataset was judged. Data were integrated using CrysAlis$^{Pro}$ software with a narrow frame algorithm. Data were subsequently corrected for absorption by the program SCALE3 ABSPACK scaling algorithm.

These structures were solved by direct method and refined using the SHELXTL 97 software suite. Atoms were located from iterative examination of difference F-maps following least squares refinements of the earlier models. Final model was refined anisotropically (if the number of data permitted) until full convergence was achieved. Hydrogen atoms were placed in calculated positions (C—H=0.93 Å) and included as riding atoms with isotropic displacement parameters 1.2-1.5 times Ueq of the attached C atoms. Highly porous crystals that contain solvent-filled pores often yield raw data where observed strong (high intensity) scattering becomes limited to ~1.0 Å at best, with higher resolution data present at low intensity. The structure was examined using the ADSYM subroutine of PLATON to assure that no additional symmetry could be applied to the models. The ellipsoids in ORTEP diagrams are displayed at the 50% probability level (FIG. 1).

Example 5

Photophysical Studies

UV-Vis spectra were obtained by using a Cary 500 scan UV-Vis-NIR spectrometer. Room temperature emission spectrum was obtained using an Edinburgh instrument Xe-900 spectro fluorometer. The fluorescence quantum yields, $\Phi_f$, were estimated by using equation 1 in water medium using the integrated emission intensity of $Ru(bpy)_3$ $Cl_2$ ($\Phi_f$=0.042 in $H_2O$ at RT) as a reference. (FIG. 20)

Lifetime Measurements

Luminescent lifetimes were obtained using a Horiba TCSPC (Time Correlated Single Photon Counting) system exciting at 443 nm. 10,000 counts were collected for each lifetime measurement and all measurements were performed in triplicate using DAS software to confirm results. The calculation of the luminescent lifetimes was performed by fitting an exponential decay function to each decay plot to extract the lifetime information using DAS6 fluorescence decay analysis software (FIG. 2).

Partition Coefficient Measurements:

n-Octanol saturated water and water saturated octanol was obtained using Millipore water stirred with n-octanol for 24 h before the two layers were separated by centrifugation (3000 rpm, 5 min). The chloride salts of complex 1 and 2 were dissolved in n-octanol saturated water giving concentrations ranging from 0.5 to 3.0 mmol. This was then mixed with water saturated n-octanol in the ratio of 1:1 (v/v). Resulting solvent mixtures were vertexed for 30 min at room temperature, and then were subjected to centrifugation (3000 rpm, 5 min) to get two distinct separate layers. Samples from each layer were obtained using a fine-gauge needle and the absorbance of respective complex in each phase determined using UV-Vis spectroscopy.

Figure 21:
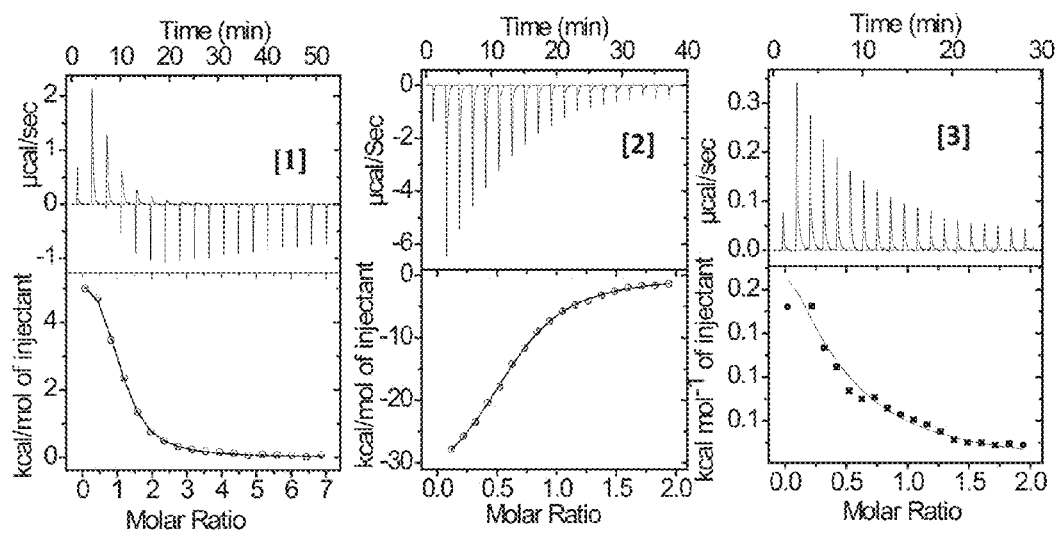
FIG. 21. ITC binding profile for the interaction of 1 (left), 2 (centered)) and 3 (right) with CT-DNA in Tris-HCl buffer pH=7.4 at 25° C.

Isothermal Titration Calorimetry (ITC) Studies:

ITC experiments were performed with the Microcal iTC200. CT-DNA (0.1 mmol) and complexes 1 (5 mmol), 2 (5 mmol) and 3 (5 mmol) were used for these experiments. All titrations were conducted in Tris-HCl buffer (5 mmol Tris and 25 mmol NaCl), pH=7.4 at 25° C. In each titration CT-DNA was loaded into the cell and 1 or 2 or 3 were taken into the syringe. Aliquot of 2 µL of compounds were injected into the cell containing DNA. In each experiment, the raw isotherms were corrected for heat of dilution by subtracting the isotherms representing the compounds injected into the Tris-HCl buffer. The resulting isotherms were fitted with the one set of site binding model provided with Microcal iTC200. (Refer FIG. 21)

Cell Viability Assays:

Cell cultures were treated with 0-350 µM solutions of 1, 2 (final medium composition=90% cell media, 10% PBS) in triplicate for 24 h. After incubation 5 µl of MTT reagent was added and incubated for 4 hrs. MTT (thiazolyl blue tetrazolium bromide) dissolved in serum-free media. After 4 h incubation the media was removed and the formazan product was eluted using isopropanol and the absorbance at 540 nm quantified by plate reader. An average absorbance for each concentration was obtained and the metabolic activity of the cell population was determined as a percentage of untreated negative control. (FIG. 13)

Microscopy:

MCF-7 and HEK293T cells were cultured in DMEM respectively supplemented with 10% FBS and penicillin/streptomycin. Cell lines were maintained at 37° C. in an atmosphere of 5% $CO_2$ and routinely sub-cultured. For CLSM, cell cultures were grown on 6 well plate with coverslips, after 24 hrs of incubation the cells were treated with solutions of 1 or 2 (20 µM,) in serum containing media and incubated for 2 h. After incubation media was removed and cells were washed with 1×PBS buffer and fixed them using paraformaldehyde and stained for confocal microscopy. Nuclear staining was performed by using DAPI. Olympus Fluoview was used to observe the compound staining Compound was excited at 443 nm and emission was detected at 620 nm wavelength.

Figure 14:
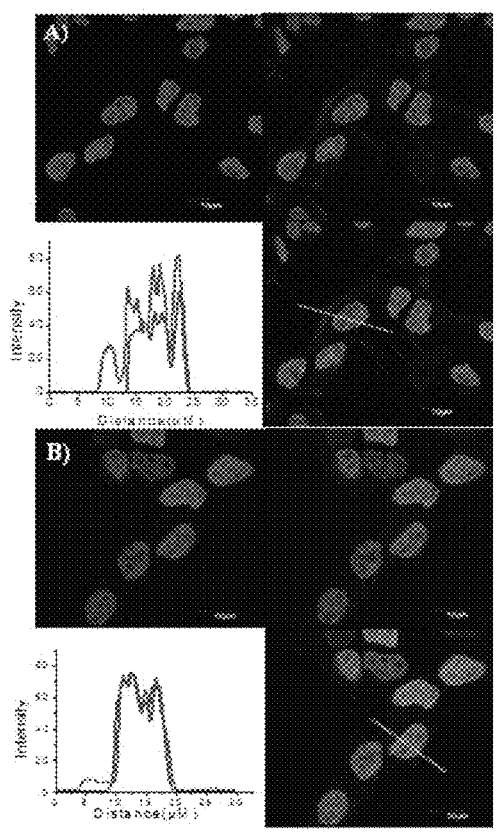
FIG. 14. Confocal image of MCF-7 cells incubated with complex 1(A) and 2(B) for 1 hr.
Figure 15:
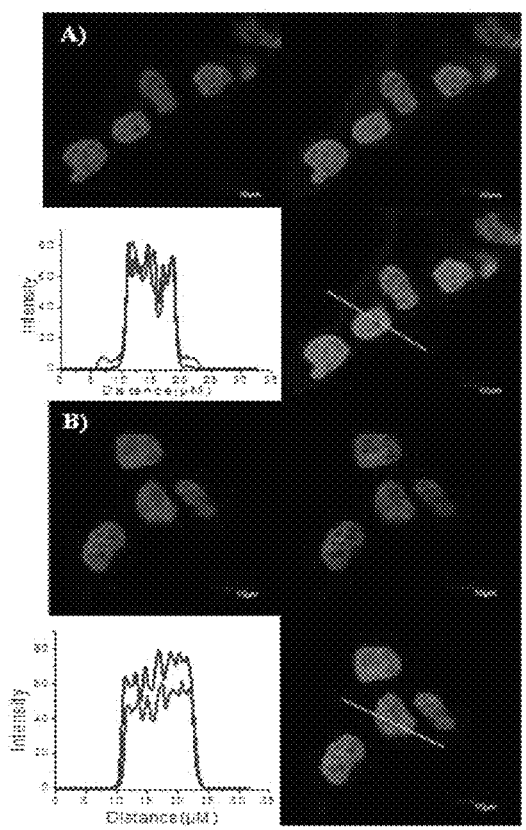
FIG. 15. Confocal image of MCF-7 cells incubated with complex 1(A) and 2(B) for 1.5 hr.
Figure 16:
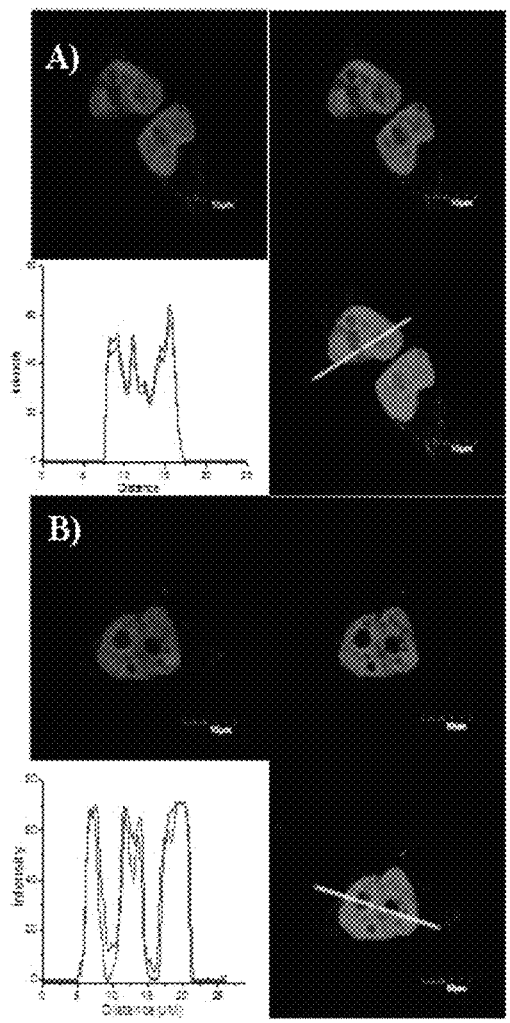
FIG. 16. HEK 293T cells incubated with complexes 1 (A), and 2(B) for 2 h.

DAPI was excited by using a 405 nm diode laser and emission detected with a 420-480 nm long-pass band-filter. (FIG. 14, 15, 16, 17)

Cellular Uptake & Quantification of 1, 2, and 3 by (MP-AES)

Cellular accumulation studies for complexes 1, 2, and 3 were conducted on the MCF-7 cell line. Briefly, $2.5 \times 10^5$-$1 \times 10^6$ cells were seeded on a petridish; the metal complexes were then added to give final concentrations of 50 µM and allowed a further 24 h of drug exposure at 37° C. After this time, cells were treated with trypsin, counted using haemocytometer, and cells collected were digested overnight in concentrated nitric acid (73%) at 60° C.; Samples were made up to exactly 10 mL using deionized water and the amount of ruthenium taken up by the cells was estimated by MP-AES (Microwave Plasma Atomic Emission Spectroscopy), using an Agilent Technologies instrument (Model No: 4100 MP-AES). The solvent used for all MP-AES experiments was double deionized water (DDW). The concentrations used for the calibration curve were in all cases 0, 5, 7.5, 10 ppm. The isotope detected was $^{101}Ru$; readings were made in duplicate ($N_2$ gas mode).

Thus the present inventors have successfully developed novel Ruthenium (II) polypyridyl complexes (1 and 2) as imaging reagents. Both the reagents were preferentially localized in lipid dense regions such as endoplasmic reticulum, cell membrane, and cytoplasmic vacuoles of live MCF-7 cells, which illustrates the role of uracil and 5-fluorouracil functionality in achieving specificity for the lipid dense regions in live cells. Relatively higher lipophilicity of complex 2 helped in achieving better cellular internalization. For fixed cell, the lipid layer disruption helped in explicit localization in cell nucleus through specific interaction with cellular DNA. Insignificant toxicity, photo-stability, visible light excitation, good solubility, high lipophilicity & permeability and large ☐☐Ss of ~160 nm being the characteristics of these two novel complexes enable their application as an imaging reagent for DNA in live cells.

|  |  | Ru accumulation |
| --- | --- | --- |
| Complex | logP | ppm/10⁶ cells |
| 1 | −0.85 | 1.5 |
| 2 | −0.50 | 2.3 |
| 3 | −1.1 | 0.8 |

TABLE 1

Crystal structure and refinement details of 2

| Empirical formula | C37 H33 F12 N9 O4 P2 Ru |
| --- | --- |
| Formula weight | 1058.73 |
| Temperature | 298 K |
| Wavelength | 0.71073 Å |
| Crystal system | monoclinic |
| Space group | C 2/c |
| Unit cell dimensions | a = 39.898(4) Å α = 90° |
|  | b = 10.0280(8) Å β = 107° |
|  | c = 22.1207(14) Å γ = 90° |
| Unit cell volume | 8462.4(13) |
| Z | 8 |
| Density (calculated) | 1.662 mg mm$^{-3}$ |
| Absorption coefficient | 0.551 |
| F(000) | 4256 |
| Crystal size | 0.3 × 0.2 × 0.2 mm³ |
| Theta range for data collection | 2.95 to 29.14 |
| Index ranges | −51 <= h <= 53, −13 <= k <= 13, −27 <= l <= 29 |
| Reflections collected | 23879 |
| Independent reflections | 22963 |
| Absorption correction | Semi-empirical from equivalents |
| Refinement method | Full-matrix least-squares on F² |
| Data/restraints/parameters | 9749/0/587 |
| Goodness-of-fit on F² | 1.606 |
| Final R indices [I >= 2sigma(I)] | $R_1$ = 0.0812, $wR_2$ = 0.1504 |
| R indices (all data) | $R_1$ = 0.1609, $wR_2$ = 0.1662 |
| Largest diff. peak and hole | 0.841 and −0.626 e · Å$^{-3}$ |

TABLE 2

Log P values obtained by using shake-flask method. Molinspiration software was used for calculation of log p values for uracil and 5-FU. (http://www.molinspiration.com/cgi-bin/properties).

| Compound | 1 | 2 | Uracil | 5-Fluorouracil |
| --- | --- | --- | --- | --- |
| LogP | −0.99 ± 0.05 | −1.59 ± 0.09 | −0.89 | −0.58 |

TABLE 3

Photophysical properties of the complexes 1, 2, and 3 recorded in pure aqueous medium.

| Complex | $\lambda_{abs}$/nm (ε/10³M$^{-1}$ cm$^{-1}$) | $\lambda_{ex}$ max/nm ($\lambda_{em}$) | $\lambda_{em}$ max/nm ($\lambda_{ex}$) | $\Phi_f$ | τ (ns) |
| --- | --- | --- | --- | --- | --- |
| 1 | 246 (18.59) | 249 |  | 0.048 | 336 |
|  | 287 (54.74) | 305 |  |  |  |
|  | 455 (9.41) | 461 (617) | 617 |  |  |
| 2 | 247 (28.08) | 232 |  | 0.050 | 323 |
|  | 287 (79.35) | 293 |  |  |  |
|  | 455 (13.85) | 461 (617) | 617 |  |  |
| 3 | 246 (18.01) | 240 |  | 0.05 | 321 |
|  | 290 (55.05) | 308 |  |  |  |
|  | 456 (14.60) | 459 (619) | 619 |  |  |

TABLE 4

ITC binding parameters for interaction of 1 and 2 with CT-DNA.

| Complex | 2 | 1 | 3 |
| --- | --- | --- | --- |
| ΔH [Kcal/M$^{-1}$] | 1.47 ± 0.02 | −35.5 ± 0.41 | 0.51 ± 0.25 |
| −TΔS [Kcal/M$^{-1}$] | 7.47 | 28.87 | 5.03 |
| ΔG [Kcal/M$^{-1}$] | −6.00 ± 0.02 | −6.68 ± 0.41 | −4.52 ± 0.25 |
| N [bp] | 0.98 ± 0.01 | 0.61 ± 0.0 | 0.354 ± 0.14 |
| $K_a$ [M$^{-1}$] | (2.51 ± 0.16) 10⁴ | (7.23 ± 0.24)10⁴ | (2.05 ± 0.85)10³ |

ADVANTAGES OF THE INVENTION a. Novel complexes
b. Simple & one step synthesis
c. Complexes are used for cellular DNA imaging.
d. Complexes are water soluble, non-toxic, good lifetime, and their fluorescence falls in visible range with large stokes shift.

We claim:

1. A Ruthenium (II) polypyridyl complex having formula I

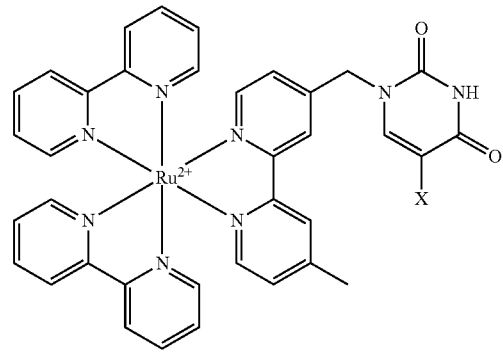

Formula I wherein, X is selected from hydrogen or fluorine.

2. A process for the preparation of a Ruthenium(II) polypyridyl complex having formula I,

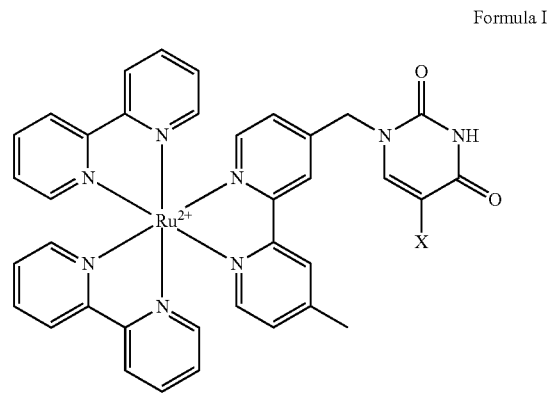

Formula I wherein, X is selected from hydrogen or fluorine comprising;

a) reacting [Ru(bpy)$_2$Cl$_2$]$^{2+}$ compound of formula 4 with the ligand of formula 3 in ethanol to form Ruthenium (II) polypyridyl complexes having formula I, wherein formula 3 and formula 4 are;

Formula 3

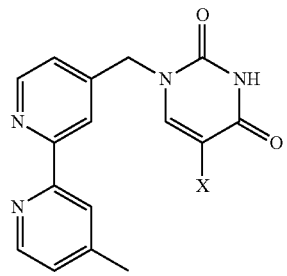

formula 4

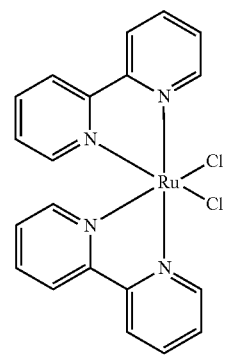

wherein, X is selected from hydrogen or fluorine, b) precipitating the Ruthenium(II) polypyridyl complexes by the addition of saturated aqueous potassium hexafluorophosphate (KPF$_6$) solution; and c) purifying the complexes having formula I.

3. The process according to claim 2, wherein, the ligand of formula 3 is selected from a) 5-fluoro-1-((4'-methyl-[2,2'-bipyridin]-4-yl)methyl)pyrimidine-2,4(1H,3H)-dione and b) 1-((4'-methyl-[2,2'-bipyridin]-4-yl)methyl)pyrimidine-2,4(1H,3H)-dione.

4. The process according to claim 2, wherein, the ligand of formula 3 is prepared by a process comprising reacting 4-(bromomethyl)-4'-methyl-2,2'-bipyridine with 5-fluorouracil or Uracil in presence of K$_2$CO$_3$ and potassium iodide in DMSO to obtain the 5-fluoro-1-((4'-methyl-[2,2'-bipyridin]-4-yl)methyl)pyrimidine-2,4(1H,3H)-dione and 1-((4'-methyl-[2,2'-bipyridin]-4-yl)methyl)pyrimidine-2,4(1H,3H)-dione, respectively.

5. A composition comprising Ruthenium (II) polypyridyl complexes of formula I along with one or more pharmaceutical carriers for use as DNA imaging agent, Formula I

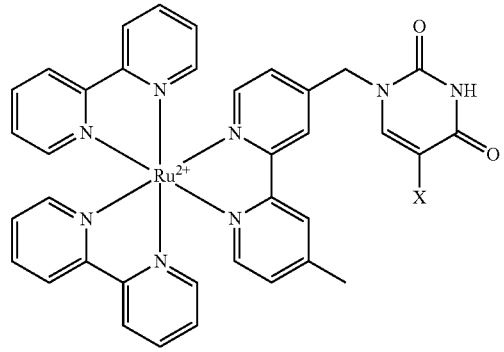

wherein, X is selected from hydrogen or fluorine.

6. A method of imaging DNA in a tumor/cancer cell lines comprising (a) Addition of an imaging agent comprising Ruthenium (II) polypyridyl complexes having formula I Formula I

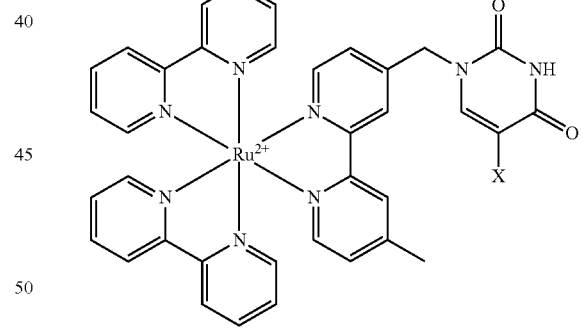

wherein, X is selected from hydrogen or fluorine, (b) subjecting/exposing the mammalian cancer cell lines to an energy source (λ=442 nm); and (c) observing the image of DNA by intracellular fluorescence intensities of the imaging agent in the cells or detecting an emission from the imaging agent in the cells using the energy source.

7. The method according to claim 6, wherein, the energy source may be selected from photon emission computed spectroscopy; positron emission tomography (PET) and the like.

8. The method according to claim 6, wherein the cancer/tumor cell may be selected from breast cancer; epithelial cancer, lung cancer, ovarian carcinoma, pancreatic carcinoma, prostate cancer or colorectal carcinoma.

9. A method of imaging DNA in a mammal, comprising:
(a) administering to the mammal an amount of a composition comprising Ruthenium (II) polypyridyl complexes having formula I

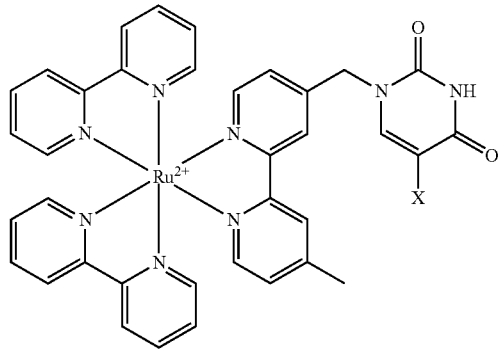

Formula I wherein, X is selected from hydrogen or fluorine (b) subjecting or exposing the mammal to an energy source ($\lambda$=442 nm); and (c) observing the image of DNA in cells of the mammal by intracellular fluorescence intensities or detecting an emission from cells of the mammal using the energy source.

10. The complex of claim 1 wherein the complex is selected from the group consisting of:

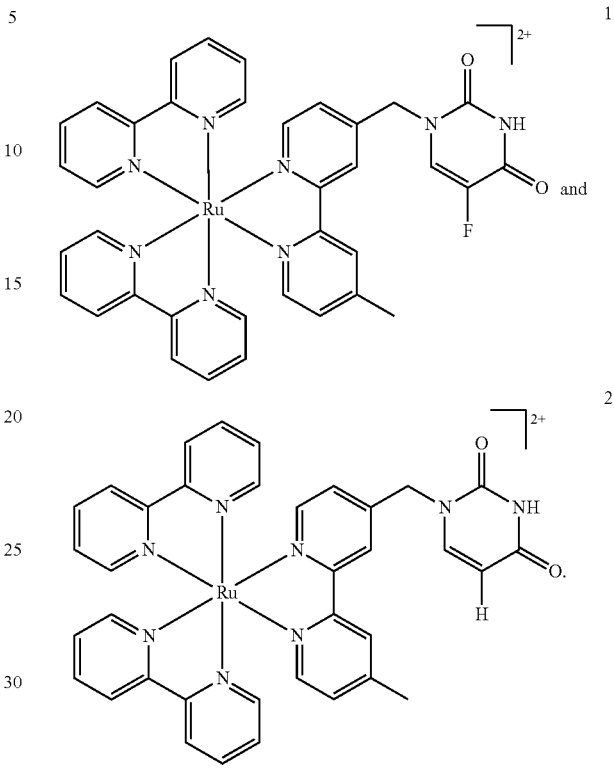

11. The Ruthenium (II) polypyridyl complex of claim 10 selected from
   a) {bis-(2,2'-bpy)-(5-fluoro-1-((4'-methyl-[2,2'-bipyridin]-4-yl)methyl)pyrimidine-2,4(1H,3H)-dione)}ruthenium(II) dichloride; and
   b) {bis-(2,2'-bpy)-(1-((4'-methyl-[2,2'-bipyridin]-4-yl)methyl)pyrimidine-2,4(1H,3H)-dione)}ruthenium(II) dichloride.

* * * * *